(12) United States Patent
Bennett et al.

(10) Patent No.: US 12,268,760 B2
(45) Date of Patent: Apr. 8, 2025

(54) COMPOSITIONS OF AND METHODS OF MAKING FERRITIN-BASED IMAGING AGENTS

(71) Applicant: Washington University, St. Louis, MO (US)

(72) Inventors: Kevin Bennett, St. Louis, MO (US); Edwin Baldelomar, St. Louis, MO (US)

(73) Assignee: Washington University, St. Louis, MO (US)

( * ) Notice: Subject to any disclaimer, the term of this patent is extended or adjusted under 35 U.S.C. 154(b) by 446 days.

(21) Appl. No.: 17/434,800

(22) PCT Filed: Mar. 5, 2020

(86) PCT No.: PCT/US2020/021122
§ 371 (c)(1),
(2) Date: Aug. 30, 2021

(87) PCT Pub. No.: WO2020/181051
PCT Pub. Date: Sep. 10, 2020

(65) Prior Publication Data
US 2022/0160906 A1    May 26, 2022

Related U.S. Application Data

(60) Provisional application No. 62/933,840, filed on Nov. 11, 2019, provisional application No. 62/814,104, filed on Mar. 5, 2019.

(51) Int. Cl.
| *A61K 51/08* | (2006.01) |
| *A61K 49/14* | (2006.01) |
| *A61P 13/12* | (2006.01) |
| *C07K 14/435* | (2006.01) |
| *C12N 15/62* | (2006.01) |

(52) U.S. Cl.
CPC .............. *A61K 51/08* (2013.01); *A61K 49/14* (2013.01); *A61P 13/12* (2018.01); *C07K 14/435* (2013.01); *C12N 15/62* (2013.01)

(58) Field of Classification Search
CPC ........ A61K 51/00; A61K 51/08; A61K 49/00; A61K 49/14; A61K 49/0002; A61K 51/1251; A61K 49/1866; A61P 13/12; C07K 14/435; C12N 15/62; H01F 1/0054; B82Y 5/00
USPC .......... 424/1.11, 1.45, 1.49, 1.65, 1.69, 1.81, 424/1.85, 9.1, 9.2
See application file for complete search history.

(56) References Cited

U.S. PATENT DOCUMENTS

| 7,763,420 B2 | 7/2010 | Stritzker et al. |
| 10,251,592 B2 | 4/2019 | Bennett et al. |

| 2004/0028694 A1 | 2/2004 | Young et al. |
| 2007/0258889 A1 | 11/2007 | Douglas et al. |
| 2008/0292545 A1 | 11/2008 | Lin et al. |

FOREIGN PATENT DOCUMENTS

| WO | 2006099516 A2 | 9/2006 |
| WO | 2015135597 A1 | 9/2015 |

OTHER PUBLICATIONS

Fan et al, Nature Nanotechnology, vol. 7, No. 7, pp. 459-464 (Year: 2012).*
Asabella et al., "The Copper Radioisotopes: A Systematic Review with Special Interest to 64Cu", BioMed Research International, 2014, v. 2014, Article ID 786463, pp. 1-9.
Baldelomar et al., "Phenotyping by magnetic resonance imaging nondestructively measures glomerular number and volume distribution in mice with and without nephron reduction", Kidney International, 2016, v. 89(2), pp. 498-505.
Baldelomar et al., "Measuring rat kidney glomerular No. and size in vivo with MRI", Am J Physiol Renal Physiol, 2017, v. 314, pp. F399-F406.
Beeman et al., "Measuring glomerular number and size in perfused kidneys using MRI", Am J Physiol Renal Physiol, 2011, v. 300(6), pp. F1454-F1457.
Beeman et al., "Toxicity, Biodistribution, and Ex Vivo MRI Detection of Intravenously Injected Cationized Ferritin", Magn. Reson. Med., 2013, v. 69, pp. 853-861.
Beeman et al., "MRI-based glomerular morphology and pathology in whole human kidneys", Am J Physiol Renal Physiol, 2014, v. 306(11), pp. F1381-F1390.
Bennett et al., "MRI of the Basement Membrane Using Charged Nanoparticles as Contrast Agents", Magn. Reson. Med., 2008, v. 60, pp. 564-574.
Bhushan et al., "Ferritin Nanocages: A Novel Platform for Biomedical Applications," Journal of Biomedical Nanotechnology, 2014, v. 10, pp. 2950-2976.
Carreira et al., "Ultra-fast stem cell labelling using cationised magnetoferritin", Nanoscale, 2016, v. 8, pp. 7474-7483.
Danon et al. "Use of cationized ferritin as a label of negative charges on cell surfaces", J. Ultra-struct. Res., 1972, v. 38, pp. 500-510.
Heger et al., "Apoferritin applications in nanomedicine," Nanomedicine, 2014, v. 9(14), pp. 2233-2245.
Lin et al., "Chimeric ferritin nanocages for multiple function loading and multimodal imaging," Nano Lett., 2011, v. 11 (2), pp. 814-819.
Sun et al., "Positron Emission Tomography Imaging Using Radiolabeled Inorganic Nanomaterials," Acc Chem Res., 2015, v. 48(2), pp. 286-294.

(Continued)

*Primary Examiner* — Jennifer Chin

(57) ABSTRACT

Among the various aspects of the present disclosure is the provision of methods and compositions for detecting recombinant cationic ferritin imaging agents. Also provided are transgenic microorganisms capable of synthesizing a recombinant ferritin imaging agent and methods of making the same. The imaging agents described herein can be used to effectively and noninvasively detect renal pathologies and are suitable for use in a number of imaging modalities.

10 Claims, 13 Drawing Sheets

Specification includes a Sequence Listing.

(56) References Cited

OTHER PUBLICATIONS

Wang et al., "Functional ferritin nanoparticles for biomedical applications," Front Chem Sci Eng., 2017, v. 11(4), pp. 633-646.
Xing et al., "Radiolabeled Nanoparticles for Multimodality Tumor Imaging", Theranostics, 2014, v. 4(3), pp. 290-306.
Zhen et al., "Ferritins as nanoplatforms for imaging and drug delivery," Expert Opin Drug Deliv. 2014, 11(12), pp. 1913-1922.

* cited by examiner

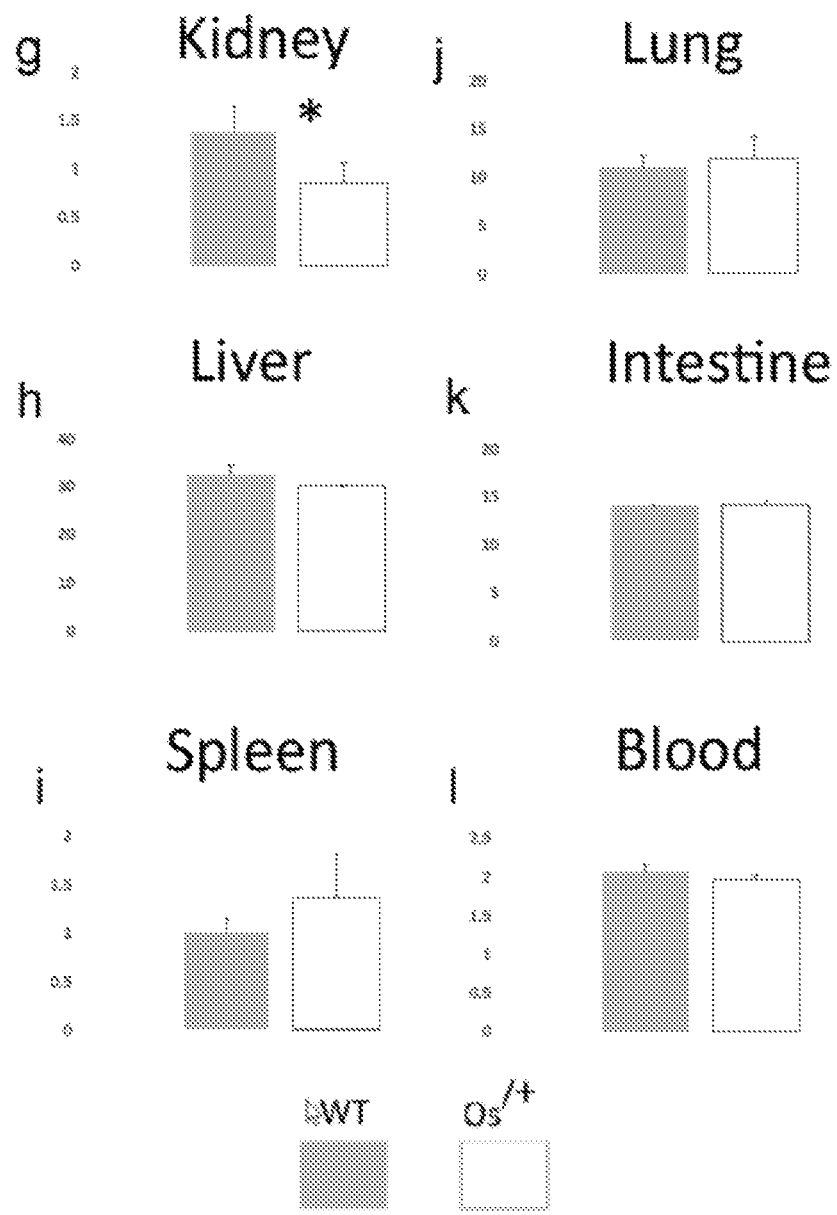

SEQUENCE LISTING

```
<160> NUMBER OF SEQ ID NOS: 4

<210> SEQ ID NO 1
<211> LENGTH: 33
<212> TYPE: DNA
<213> ORGANISM: Artificial Sequence
<220> FEATURE:
<223> OTHER INFORMATION: synthetic primer

<400> SEQUENCE: 1
```

```
gacaagcata tgacgaccgc gtccacctcg cag                          33

<210> SEQ ID NO 2
<211> LENGTH: 39
<212> TYPE: DNA
<213> ORGANISM: Artificial Sequence
<220> FEATURE:
<223> OTHER INFORMATION: synthetic primer

<400> SEQUENCE: 2
gcctccgtcg acttagcttt cattatcact gtctcccag                    39

<210> SEQ ID NO 3
<211> LENGTH: 57
<212> TYPE: DNA
<213> ORGANISM: Artificial Sequence
<220> FEATURE:
<223> OTHER INFORMATION: synthetic primer

<400> SEQUENCE: 3
gcctcagtcg acgaggagat aacatatgag ctcccagatt cgtcagaatt attccac    57

<210> SEQ ID NO 4
<211> LENGTH: 43
<212> TYPE: DNA
<213> ORGANISM: Artificial Sequence
<220> FEATURE:
<223> OTHER INFORMATION: synthetic primer

<400> SEQUENCE: 4
cacgatgaat tcttattagt cgtgcttgag agtgagcctt tcg               43
```

COMPOSITIONS OF AND METHODS OF MAKING FERRITIN-BASED IMAGING AGENTS

CROSS-REFERENCE TO RELATED APPLICATIONS

This application claims the benefit of priority to PCT International Application No. PCT/US20/21122 filed on 5 Mar. 2020, which claims the benefit of priority from U.S. Provisional Application Ser. No. 62/814,104 filed on 5 Mar. 2019 and 62/933,840 filed on 11 Nov. 2019, which are incorporated herein by reference in their entireties.

STATEMENT REGARDING FEDERALLY SPONSORED RESEARCH OR DEVELOPMENT

This invention was made with government support under DK111861 awarded by the National Institutes of Health. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to ferritin-based imaging agents and methods of making and detection thereof.

SUMMARY OF THE INVENTION

Among the various aspects of the present disclosure is the provision of methods and compositions for making imaging agents comprising ferritin-based (e.g., human recombinant ferritin fusion proteins) nanoparticles.

For example, the present disclosure provides for imaging agents that have use as positron emission tomography (PET) imaging agents and/or MRI contrast agents. Compositions and methods of generating and using these imaging agents are also provided.

In some embodiments, the imaging agent comprises (a) a ferritin or an apoferritin cage (ferritin cage or shell without a core), and optionally a magnetic core, and/or (b) a radiolabeled ferritin or radiolabeled apoferritin, wherein the ferritin or apoferritin can be cationic and/or recombinant.

Other aspects of the present invention are directed to processes of preparing an imaging agent. In some embodiments, the process comprises complexing a radioisotope with cationic ferritin-based nanoparticle comprising a functionalized apoferritin-based nanoparticle cage and, optionally, a magnetic core in reaction mixture to form the imaging agent, wherein the functionalized apoferritin cage can comprise a cationic crosslinker, capable of accumulating in kidney nephrons or the glomerular basement membrane.

Further aspects of the present invention are directed to methods of imaging a target in a subject. In some embodiments, the method comprises administering the imaging agent as described or prepared herein to the subject and imaging using magnetic resonance imaging (MRI) and/or positron emission tomography (PET).

Another aspect of the present disclosure provides for an imaging agent comprising: a recombinant ferritin fusion protein comprising at least one heavy chain subunit of ferritin and, optionally, at least one light chain subunit of ferritin; and a magnetic nanoparticle core, wherein the magnetic nanoparticle core is bound within the recombinant ferritin fusion protein; or a positron emitting isotope bound within the recombinant ferritin fusion protein. In some embodiments, the imaging agent comprises a magnetic nanoparticle core. In some embodiments, the imaging agent comprises a positron emitting isotope. In some embodiments, the imaging agent comprises a magnetic nanoparticle core and a positron emitting isotope. In some embodiments, the magnetic nanoparticle core comprises iron. In some embodiments, the magnetic nanoparticle core comprises iron oxide. In some embodiments, the recombinant ferritin fusion protein is a human or horse recombinant ferritin fusion protein. In some embodiments, the recombinant ferritin fusion protein is a cationic recombinant ferritin fusion protein. In some embodiments, the cationic recombinant ferritin fusion protein comprises a cationic crosslinker. In some embodiments, the cationic crosslinker comprises an amine ion or a $C_1$ to $C_{20}$ organic compound having one to four amine functional groups. In some embodiments, the cationic crosslinker comprises a tertiary or a primary amine group. In some embodiments, the surface of the magnetic nanoparticle core or an inner surface of the recombinant ferritin fusion protein is radiolabeled with a radioisotope. In some embodiments, the radioisotope is a synthetic radioisotope. In some embodiments, the radioisotope is selected from $^{64}Cu$, $^{68}Ga$, $^{86}Y$, $^{89}Zr$, and $^{124}I$. In some embodiments, the radioisotope is selected from $^{64}Cu$. In some embodiments, the imaging agent is a contrast agent or a radioimaging agent. In some embodiments, the imaging agent is a magnetic resonance imaging (MRI) contrast agent, a positron emission tomography (PET) imaging agent, a single-photon emission computerized tomography (SPECT) imaging agent, or a PET-MRI imaging agent. In some embodiments, the recombinant ferritin fusion protein is synthesized by a transgenic microorganism. In some embodiments, the imaging agent has a diameter of about 30 nm or less, about 25 nm or less, about 20 nm or less, about 15 nm or less, about 14 nm or less, about 13 nm or less, about 12 nm or less, about 11 nm or less, or about 10 nm or less. In some embodiments, the magnetic nanoparticle core has a diameter of about 20 nm or less, about 15 nm or less, about 10 nm or less, about 5 nm or less, about 4 nm or less, about 3 nm or less, about 2 nm or less, or about 1 nm or less. In some embodiments, the imaging agent is capable of accumulating in a glomerular basement membrane of a subject or a tissue when administered to the subject.

Another aspect of the present disclosure provides for a method of measuring nephron endowment in a subject comprising administering the imaging agent described herein in an amount effective to produce contrast in a magnetic resonance image or a positron emission tomography (PET) image in the subject. In some embodiments, measuring nephron endowment is performed in a subject having, suspected of having, or at risk for a renal pathology, disease, or disorder; a donor; a human allograft; a post-transplant patient; a subject having or being at risk for having renal effects from a drug; a subject having or at risk for kidney disease wherein the subject does not exhibit either gross proteinuria or changes in glomerular filtration rate (GFR); or a subject having, suspected of having, or at risk for acute kidney injury. In some embodiments, the imaging agent comprises the magnetic nanoparticle core. In some embodiments, the imaging agent comprises the positron emitting isotope. In some embodiments, the imaging agent comprises the magnetic nanoparticle core and the positron emitting isotope. In some embodiments, the magnetic nanoparticle core comprises iron. In some embodiments, the magnetic nanoparticle core comprises iron oxide. In some embodiments, the recombinant ferritin fusion protein is a human or horse recombinant ferritin fusion protein. In some embodiments, the recombinant ferritin fusion protein is a cationic recombinant ferritin fusion protein. In some embodiments, the cationic recombinant ferritin fusion protein comprises a cationic crosslinker. In some embodiments, the cationic crosslinker comprises an amine ion or a $C_1$ to $C_{20}$ organic compound having one to four amine functional groups. In some embodiments, the cationic crosslinker comprises a tertiary or a primary amine group. In some embodiments, the surface of the magnetic nanoparticle core or an inner surface of the recombinant ferritin fusion protein is radiolabeled with a radioisotope. In some embodiments, the radioisotope is a synthetic radioisotope. In some embodiments, the radioisotope is selected from $^{64}Cu$, $^{68}Ga$, $^{86}Y$, $^{89}Zr$, and $^{124}I$. In some embodiments, the radioisotope is selected from $^{64}Cu$. In some embodiments, the imaging agent is a contrast agent or a radioimaging agent. In some embodiments, the imaging agent is a magnetic resonance imaging (MRI) contrast agent, a positron emission tomography (PET) imaging agent, a single-photon emission computerized tomography (SPECT) imaging agent, or a PET-MRI imaging agent. In some embodiments, the recombinant ferritin fusion protein is synthesized by a transgenic microorganism. In some embodiments, the imaging agent has a diameter of about 30 nm or less, about 25 nm or less, about 20 nm or less, about 15 nm or less, about 14 nm or less, about 13 nm or less, about 12 nm or less, about 11 nm or less, or about 10 nm or less. In some embodiments, the magnetic nanoparticle core has a diameter of about 20 nm or less, about 15 nm or less, about 10 nm or less, about 5 nm or less, about 4 nm or less, about 3 nm or less, about 2 nm or less, or about 1 nm or less. In some embodiments, the imaging agent is capable of accumulating in a glomerular basement membrane of a subject or a tissue when administered to the subject.

Another aspect of the present disclosure provides for a method of imaging a target in a subject comprising administering the imaging agent of described herein in an amount effective to produce contrast in a magnetic resonance image or a positron emission tomography image. In some embodiments, the method comprises imaging the target using magnetic resonance imaging. In some embodiments, the method comprises imaging the target using positron emission tomography. In some embodiments, the target comprises a kidney or a kidney cell. In some embodiments, the target comprises a nephron or a renal glomerulus. In some embodiments, the subject has, is suspected of having, or at risk for having a renal pathology, disease, or disorder. In some embodiments, the subject has, is suspected of having, or is at risk for chronic kidney disease (CKD). In some embodiments, the imaging agent comprises the magnetic nanoparticle core. In some embodiments, the imaging agent comprises the positron emitting isotope. In some embodiments, the imaging agent comprises the magnetic nanoparticle core and the positron emitting isotope. In some embodiments, the magnetic nanoparticle core comprises iron. In some embodiments, the magnetic nanoparticle core comprises iron oxide. In some embodiments, the recombinant ferritin fusion protein is a human or horse recombinant ferritin fusion protein. In some embodiments, the recombinant ferritin fusion protein is a cationic recombinant ferritin fusion protein. In some embodiments, the cationic recombinant ferritin fusion protein comprises a cationic crosslinker. In some embodiments, the cationic crosslinker comprises an amine ion or a $C_1$ to $C_{20}$ organic compound having one to four amine functional groups. In some embodiments, the cationic crosslinker comprises a tertiary or a primary amine group. In some embodiments, the surface of the magnetic nanoparticle core or an inner surface of the recombinant ferritin fusion protein is radiolabeled with a radioisotope. In some embodiments, the radioisotope is a synthetic radioisotope. In some embodiments, the radioisotope is selected from $^{64}Cu$, $^{68}Ga$, $^{86}Y$, $^{89}Zr$, and $^{124}I$. In some embodiments, the radioisotope is selected from $^{64}Cu$. In some embodiments, the imaging agent is a contrast agent or a radioimaging agent. In some embodiments, the imaging agent is a magnetic resonance imaging (MRI) contrast agent, a positron emission tomography (PET) imaging agent, a single-photon emission computerized tomography (SPECT) imaging agent, or a PET-MRI imaging agent. In some embodiments, the recombinant ferritin fusion protein is synthesized by a transgenic microorganism. In some embodiments, the imaging agent has a diameter of about 30 nm or less, about 25 nm or less, about 20 nm or less, about 15 nm or less, about 14 nm or less, about 13 nm or less, about 12 nm or less, about 11 nm or less, or about 10 nm or less. In some embodiments, the magnetic nanoparticle core has a diameter of about 20 nm or less, about 15 nm or less, about 10 nm or less, about 5 nm or less, about 4 nm or less, about 3 nm or less, about 2 nm or less, or about 1 nm or less. In some embodiments, the imaging agent is capable of accumulating in a glomerular basement membrane of a subject or a tissue when administered to the subject.

Another aspect of the present disclosure provides for a transgenic microorganism comprising an artificial DNA construct comprising, as operably associated components in the 5' to 3' direction of transcription: (i) a promoter functional in the transgenic microorganism; (ii) a first polynucleotide sequence encoding a ferritin heavy chain polypeptide or a functional variant or a functional fragment thereof; (iii) a second polynucleotide sequence encoding an internal ribosome entry site (IRES); and (iii) a third polynucleotide sequence encoding a ferritin light chain polypeptide or a functional variant or a functional fragment thereof. In some embodiments, the transgenic microorganism is capable of accumulating an assembled recombinant ferritin fusion protein. In some embodiments, the ferritin heavy chain polypeptide and the ferritin light chain polypeptide are co-expressed as a fusion protein by the transgenic microorganism. In some embodiments, the transgenic microorganism is *E. coli*.

Another aspect of the present disclosure provides for a method of producing a recombinant cationic ferritin fusion protein imaging agent, comprising: (i) providing the transgenic microorganism described herein; (ii) contacting the transgenic microorganism with a solution comprising a metal capable of binding a recombinant ferritin fusion protein comprising at least one heavy chain and at least one heavy chain or light chain region of ferritin; (iii) purifying a recombinant ferritin fusion protein product from the transgenic microorganism; and (iv) cationizing the recombinant ferritin fusion protein product to generate a recombinant cationic ferritin protein product. In some embodiments, the solution comprising a metal capable of binding a recombinant ferritin fusion protein is ferric ammonium sulfate at a concentration of between about 500 mM and about 20 mM $Fe^{3+}$. In some embodiments, the solution comprising a metal is adjusted to a pH effective to open the recombinant ferritin fusion protein. In some embodiments, the solution comprising a metal comprises a radiolabel. In some embodiments, the method comprises cationizing the recombinant ferritin fusion protein. In some embodiments, the recombinant ferritin fusion protein the recombinant ferritin fusion protein comprises at least one heavy chain, optionally a light chain, or a heavy chain and a light chain of ferritin.

Another aspect of the present disclosure provides for a method of imaging a recombinant cationic ferritin nanoparticle comprising: providing the imaging agent described herein; and administering the imaging agent to a tissue or a subject intravenously, wherein the imaging agent is capable of providing contrast in a magnetic resonance image (MRI) or a positron emission tomography (PET) image.

Another aspect of the present disclosure provides for a method of imaging a recombinant cationic ferritin fusion protein nanoparticle comprising: providing the imaging agent described herein comprising a radiolabel; and administering the imaging agent to a tissue or a subject intravenously, wherein the imaging agent provides a positron emission tomography (PET) image, a single photon emission computed tomography (SPECT) image, or a PET-MR image.

Another aspect of the present disclosure provides for an imaging agent comprising a recombinant cationic ferritin fusion protein produced by the methods described herein.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 9A-FIG. 9D show representative PET images of whole mice (A, B) and isolated renal cortex (C, D). FIG. 9E-FIG. 9F are graphs depicting signal distribution, area under the curve, and biodistribution.

FIG. 11A-FIG. 11L shows bar graphs (A-L) depicting the bio-distribution of radioCF in WT (grey) or $Os^{/+}$ mice (white) as either % ID/g (A-F) or % ID/organ (G-L) in kidney (A, G), liver (B, H), spleen (C, I), lung (D, J), intestine (E, K), and blood (F, L).

Corresponding reference characters indicate corresponding parts throughout the drawings.

DETAILED DESCRIPTION OF THE INVENTION

Figure 1A:
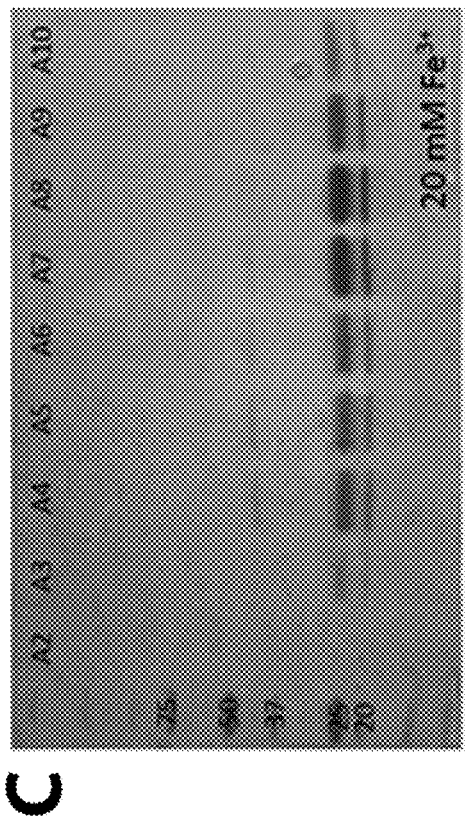
FIG. 1A-FIG. 1D is a series of images depicting the successful production of human recombinant ferritin by bacteria. Expression and purification of human H-L holo-ferritin in *E. coli* is shown. (A) Purified lysates from liquid culture after induced expression of human ferritin, with four batches of varying concentrations of ferric ammonium citrate, showing clear incorporation of iron into the lysate. (B) Extracted ferritin in all eluents ran at a similar rate in size exclusion chromatography, consistent with fully formed ferritin at 475,000 Daltons. (C-D) SDS-PAGE in eluents at all levels of iron addition in the growth medium indicated the presence of both H- and L-subunits consistent with the known size of the ferritin subunits. Each band corresponds to a separate culture and purification, indicating reproducible expression.
Figure 1B:
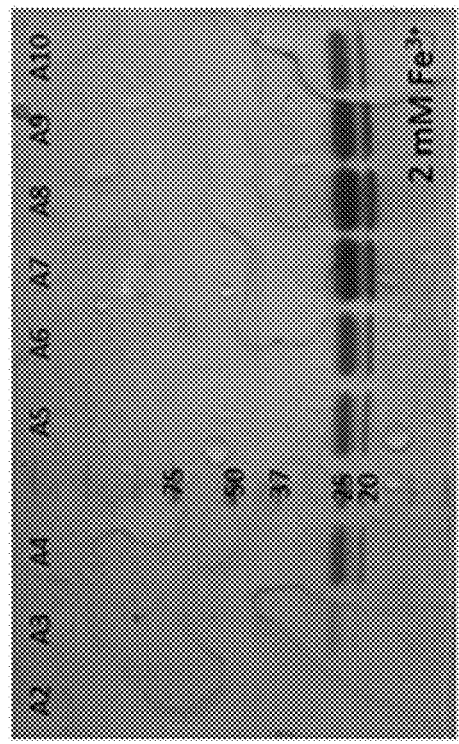
Figure 1C:
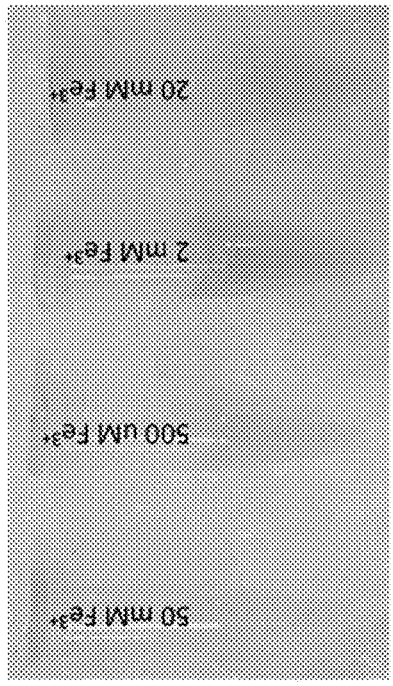
Figure 1D:
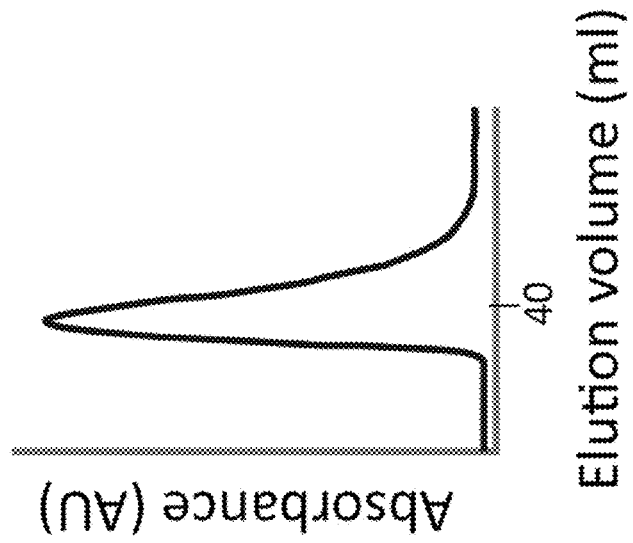

The present disclosure is based, at least in part, on the discovery that a human recombinant form of cationic ferritin (HrCF) can be used as a natural iron-oxide nanoparticle MRI contrast agent for renal imaging and/or as a PET imaging agent with or without a magnetic core. As shown herein, HrCF can be expressed, self-assembled, and loaded with iron in *E. coli* to form a ferritin nanoparticle capable of being catonized. The cationic ferritin nanoparticle can then be used for quantitative, biocompatible, and targeted contrast or imaging agent for renal imaging.

The compositions and methods described herein can be used for imaging a target using positron emission tomography (PET) and/or magnetic resonance imaging (MRI). Specifically, the imaging agents described herein have been designed to be capable of containing a positron-emitting isotope suitable for PET and/or a magnetic core to allow for MRI imaging.

Disclosed herein is the synthesis of cationic ferritin (CF) labeled with a positron-emitting isotope (e.g., Cu-64, Zr-89) that is detectable in positron emission tomography (PET). The resulting imaging agent can be used as a combined PET-MRI agent, and thus can inform early bio-distribution and toxicity studies for cationized ferritin (CF) enhanced MRI (CFE-MRI). While PET does not offer the exquisite spatial resolution and adjustable tissue contrast of MRI, it has the distinct advantage of allowing detection of agents in doses below those considered trace quantities in the US FDA requirements for an exploratory investigational new drug (IND) approach. RadioCF-PET may be rapidly translated to early clinical use, and may provide a useful surrogate for nephron endowment in humans or human tissue (e.g., donor kidneys, patients).

The present disclosure provides for Good Manufacturing Practice (GMP) production for clinical use including transplant evaluation, monitoring patients post-transplant, detecting kidney health in patients with or at risk of chronic kidney disease, and monitoring renal effects of drugs. HrCF is superior to other methods because it is presently believed to have a lower risk of toxicity in humans and it can be synthesized with high repeatability.

Also disclosed herein is a general approach to forming an iron oxide core in a recombinant ferritin molecule in bacteria, allowing for rapid synthesis of a functional imaging agent for renal imaging. For clinical translation, HrCF may overcome limitations in contrast agent biocompatibility as it is an endogenous protein regularly present in systemic circulation and in cells. It is presently thought that described herein is the first report of a human-based recombinant fusion protein, targeted nanoparticle imaging agent for quantitative renal imaging.

While previous studies have described the formation of recombinant human ferritin that use either heavy or light chain separately, described herein is a heavy and light chain fusion protein formed from constitutive expression in a transgenic microorganism, allowing the protein to take up iron similarly to the endogenous protein in vivo. This allows for more controlled loading of iron and better performance in vivo after injection. It is presently thought that recombinant human apoferritin or ferritin in any form has not been functionalized for use as an intravenously injectable targeted imaging agent.

Because the heavy chain (HC)-light chain-(LC) ferritin fusion protein had never been expressed in *E. coli*, it was unclear if it would self-assemble in the bacteria to form a natural 24mer human recombinant molecule. However, recombinant human ferritin was readily expressed and purified from *E. coli*. First, recombinant human fusion protein was attempted to be formed by expressing apoferritin in *E. coli* under low iron conditions. This would allow for loading the core with an iron oxide and the radiolabel at a later time. However, it was discovered that 1) *E. coli* grew too slowly for sufficient yield under these conditions, and 2) the number of processing steps was untenable for translation to a GMP process. However, it was unclear if the iron oxide nanoparticle could be formed in *E. coli* naturally. First, it was attempted to cause the bacteria to incorporate iron from a medium enriched by adding ferric citrate, which mammalian cells normally would take up and incorporate into the ferritin core. Surprisingly, this did not result in any iron filled ferritin, which, as discovered here, was because bacteria do not have the same mechanism for iron incorporation. Ferrous citrate was then used, which resulted in the disclosed invention. The molecule was then cationized and characterized as described herein. The advantage of the disclosed methods are that the recombinant fusion protein can be rapidly performed in GMP conditions with few steps, the iron oxide core can be detected by MRI, and the molecule can be modified to incorporate a radiolabel.

It was surprising and unexpected that the cationic fusion protein or the cationic protein itself would be capable of being radiolabeled due to its positively charged surface. As such, it was an initial concern that cationized ferritin would not incorporate the radiolabel into the cationic core because of the cationic surface. Cu-64, for example, is also cationic, so there was concern that the radiolabel would experience charge repulsion. Under the correct synthesis conditions, however, it was demonstrated that it was possible to incorporate and purify the radiolabeled protein or fusion protein with no outer surface binding of the radiolabel. It was also discovered that the radiolabeled recombinant CF had similar physical properties (charge, shape, and hydrodynamic radius) as observed in non-radiolabeled CF.

Ferritin is a large molecular weight protein involved in iron metabolism and storage. Mammalian ferritin is a 24mer, composed of heavy (H)- and light (L)-subunits and a hollow core and a ferroxidase site on the H-chain, allowing for deposition of metals and formation of a nanocrystal inside the 13 nm diameter protein. With surface functionalization, the ferritin nanoparticle can function as a versatile container for targeted drug delivery or diagnostics. In particular, ferritin has been developed as a contrast agent for magnetic resonance imaging by controlled metal deposition in the core. It has also been proposed as a gene reporter for MRI. One potential advantage of ferritin as an injectable agent is that it can be expressed recombinantly in human form, making it possible to apply for human use.

Recently, cationic ferritin (CF) has been employed as a targeted MRI contrast agent to provide quantitative maps of human nephron number and glomerular size in the kidney. CF is formed by conjugating the ferritin molecule with a cationic ligand. After intravenous injection, CF traverses the glomerular basement membrane (GBM) and binds transiently to the constituent anionic proteoglycans. With sufficient CF accumulation in the GBM, individual glomeruli can be detected and measured using MRI. Kidney glomerular number and size are strongly linked to renal and cardiovascular health and knowing nephron endowment enables new investigations into development of chronic kidney disease, developmental impacts of acute kidney injury, and transplant viability.

Nephrons

As described herein, the methods provided herein provide for measuring nephron endowment, estimating nephron mass, or detecting nephron heterogeneity throughout the kidney. Nephrons are the functional units of the kidney responsible for maintaining blood electrolyte homeostasis and osmolarity. Nephron endowment is thought to be a strong predictor of renal capacity and health. At full-term, humans are born with a full complement of nephrons, but nephron number ranges from ~200,000 to over 2,000,000 between individuals. This range may in part explain variability in susceptibility to chronic kidney and cardiovascular disease throughout life. Nephron loss can occur with aging or due to injury. Premature infants, for example, are susceptible to renal damage and nephron loss due to common nephrotoxic medications. Loss of nephrons can lead to short-term compensation of other nephrons, through hyperfiltration, to maintain glomerular filtration rate. This compensatory hyperfiltration is thought to result in further nephron loss due to damage to the remaining renal glomeruli and tubules, leading eventually to kidney disease and end stage renal disease requiring dialysis or transplant.

Nephron loss is a primary feature of chronic kidney disease that affects approximately 15% of the world population, including in the USA. Current techniques to monitor nephron number in humans can be inaccurate or destructive (e.g., serum creatinine or biopsy). Much of the understanding of the role of nephron number in human health has been achieved through postmortem analysis using stereological techniques. While these are crucially important, they are destructive and cannot be applied in vivo. Because of the impact of chronic kidney disease (CKD), it is critical to establish new diagnostic tools to understand and monitor nephron endowment in patients at risk for CKD or in transplant recipients.

Ferritin-Based Imaging Agent

Described herein is the synthesis and use of a ferritin-based imaging agent. As an example, the ferritin-based imaging agent can comprise ferritin, apoferritin, a human recombinant ferritin fusion protein, or any other functional fragment or variant of ferritin or apoferritin having iron binding and/or isotope binding capability. As another example, the imaging agent can be a contrast agent (e.g., MRI) or a radioimaging agent (e.g., PET, SPECT).

For example, the ferritin imaging agent can be a contrast agent based on apoferritin (e.g., the protein, a fusion protein, or a functional variant thereof), with or without iron in the core, that can be loaded with a radioisotope (e.g., Cu-64) and functionalized on its surface to confer a positive charge. The positive charge allows the agent to bind transiently to the glomerular basement membrane (GBM) in the kidney. The binding of the ferritin-based imaging agent to the glomerular basement membrane can be used in conjunction with MRI and/or PET to determine whole kidney nephron endowment. It is noted that the glomerular basement membrane only represents about 5% of the kidney. As such, the present disclosure provides for compositions and methods sensitive enough for imaging glomerular or nephron endowment, density, or numbers.

As described herein, the ferritin-based imaging agent can comprise (a) recombinant ferritin comprising a recombinant apoferritin cage and, optionally, a magnetic core and/or (b) a radioisotope complexed with the recombinant ferritin. As an example, the ferritin-based imaging agent can comprises cationic recombinant ferritin comprising a functionalized recombinant apoferritin cage wherein the functionalized recombinant apoferritin cage comprises a cationic crosslinker (e.g., an amine ion). For example, the cationic crosslinker can comprise amine groups. As another example, the cationic crosslinker can comprise two or more amine functional groups. As another example, the cationic crosslinker can comprise from one to four amine functional groups. As another example, the cationic crosslinker comprises a $C_1$ to $C_{20}$ organic compound having one to four amine functional groups (e.g., N,N-dimethyl-1,3-propanediamine (DMPA)).

As described herein, the magnetic core can comprise iron oxide.

The imaging agent can be characterized using standard techniques in the art. For example, the hydrodynamic radius of the imaging agent can be assessed using dynamic light scattering (DLS), zeta potentiometry can be used to measure charge and electron microscopy can be used to assess overall structure.

In various embodiments, the imaging agent has a diameter between about 2 nm and about 100 nm. For example, the imaging agent has a diameter of about 30 nm or less, about 25 nm or less, about 20 nm or less, about 15 nm or less, about 14 nm or less, about 13 nm or less, about 12 nm or less, about 11 nm or less, or about 10 nm or less. In some embodiments, the magnetic nanoparticle core has a diameter of about 20 nm or less, about 15 nm or less, about 10 nm or less, about 5 nm or less, about 4 nm or less, about 3 nm or less, about 2 nm or less, or about 1 nm or less. In various embodiments, the hydrodynamic radius of the imaging agent can be between about 2 nm and about 50 nm. For example, the hydrodynamic radius of the imaging agent can be about 50 nm or less, about 40 nm or less, about 30 nm or less about 25 nm or less, or about 20 nm or less. For example, the hydrodynamic radius of the imaging agent can be from about 2 nm to about 5 nm, 5 nm to about 50 nm, from about 5 nm to about 40 nm, from about 5 nm to about 30 nm, from about 10 nm to about 50 nm, from about 10 nm to about 40 nm, or from about 10 nm to about 30 nm. Recitation of each of these discrete values is understood to include ranges between each value. Recitation of each range is understood to include discrete values within the range.

Recombinant Ferritin Fusion Protein

As described herein, the recombinant ferritin imaging agent can be a recombinant ferritin fusion protein molecule with or without iron in the core. The recombinant ferritin can also be loaded with a radioisotope (e.g., Cu-64, Zr-89).

Ferritin is a large molecular weight protein involved in iron metabolism and storage. Mammalian ferritin typically comprises 24 peptide subunits, composed of heavy and light chain subunits that assemble to form a hollow spherical shell or cage around a nanoparticle core. A ferroxidase site on the heavy chain subunit allows for deposition of metals and formation of a nanocrystal inside the protein.

In natural ferritin, channels or pores are formed at the intersection of three peptide subunits (three-fold channels) or four peptide subunits (four-fold channels). The three-fold channels are lined with polar amino acids and are thus hydrophilic, while the hydrophobic four-fold channels are lined with non-polar residues. Although the exact mechanism is unknown, it is presently thought that $Fe^{2+}$ is loaded into the core through the three-fold channels and oxidized into $Fe^{3+}$ by bimolecular oxygen that enters through the four-fold channels. In this manner, the spherical shell or cage can be loaded with up to 4500 iron molecules, most typically stored in the form of a $Fe^{3+}$ crystalline solid known as superparamagnetic crystalline ferric oxyhydroxide (e.g., ferrihydrite).

Here, the recombinant ferritin fusion protein can be generated in a cell and the cell culture medium can be loaded with a metal such as iron to form an iron oxide core. It can be possible to use any form of iron that can provide contrast in an MRI image. The human recombinant ferritin fusion protein molecules shown here incorporated about 250 iron atoms per ferritin molecule (the iron core within a human recombinant ferritin fusion protein can be about 13 nm in diameter or larger).

In some embodiment, the recombinant ferritin fusion protein can have a diameter between about 10 nm and about 30 nm. For example, the recombinant ferritin fusion protein can have a diameter of about 30 nm or less, about 25 nm or less, about 20 nm or less, about 15 nm or less, about 14 nm or less, about 13 nm or less, about 12 nm or less, about 11 nm or less, about 10 nm or less, or about 5 nm or less. Recitation of each of these discrete values is understood to include ranges between each value. Recitation of each range is understood to include discrete values within the range.

As described herein, the ferritin imaging agent can comprise a recombinant ferritin fusion protein (e.g., a human recombinant ferritin (HrF) fusion protein), such as a functional variant thereof, having ferritin activity (e.g., ferroxidase activity). As an example, the ferritin imaging agent can comprise a human recombinant cationic ferritin protein (HrCF) or functional variant thereof. As another example, the ferritin imaging agent can comprise a recombinant ferritin fusion protein with the iron core (e.g., apoferritin recombinant fusion protein).

As described herein, a recombinant ferritin fusion protein can be generated in a cell and the cell culture medium can be loaded with a metal such as iron to form an iron oxide core. It can be possible to use any form of iron that can provide contrast in an MRI image or incorporate a radiolabel. The recombinant ferritin molecules shown here incorporated about 250 iron atoms per ferritin molecule. The recombinant ferritin can have anywhere between zero and about 4500 iron atoms. It is usual for the recombinant ferritin to comprise about 100 to 300 iron atoms. It is presently believed that the iron oxide core can comprise a mixed maghemite/magnetite core to form a magnetoferritin or a recombinant magnetoferritin.

Other mammalian ferritin or HC/LCs thereof can be used, if purified. But the HrCF is preferred as, over multiple injections, using human recombinant ferritin can reduce the likelihood of immune complex formation in the glomerulus.

As described herein, the protein subunits of a ferritin can comprise a light chain (LC) subunit and/or a heavy chain (HC) subunit (or combinations of heavy chain or light chain subunits), wherein a LC subunit has an apparent molecular weight of about 19 kDa and a HC subunit has an apparent molecular weight of about 21 kDa. HC and LC subunits may be present at different ratios within the assembled ferritin protein, and the specific ratio of HC to LC subunits typically varies between different tissues. HC subunits (and the imaging agent herein) can have ferroxidase activity and are capable of oxidizing ferrous iron ($Fe^{2+}$) to ferric iron ($Fe^{3+}$) for storage in the metal core of the protein. While the exact function of LC subunits is currently unknown, it is presently thought that LC subunits may function in electron transfer across the spherical protein shell and facilitate iron storage.

As described herein, the human recombinant ferritin fusion protein can comprise at least one heavy chain ferritin subunit and, optionally, at least one light chain ferritin subunit (or functional fragment or variant thereof). Heavy and light chain ferritin subunits are well-known in the art. As such, heavy and light chain ferritin subunits can be any known ferritin HC or LC subunit or functional variant or functional fragment thereof. A functional fragment or variant thereof can be any functional variant or fragment of HC or LC units of ferritin having ferroxidase activity, metal (e.g., iron) binding activity and/or capable of providing contrast in an MRI image.

As described herein, a heavy and light chain fusion protein can be formed from constitutive expression in a transgenic microorganism (see e.g., Example 1 and Example 2), allowing for the production of a human recombinant ferritin fusion protein that can bind iron similarly to endogenous ferritin or ferritin found in nature. Polynucleotide sequences for encoding HC and LC subunits are commercially available or can be generated by known methods in the art.

Nanoparticle Core

As described herein, the recombinant ferritin (e.g., human recombinant ferritin (HrF)) fusion protein can form a cage around a nanoparticle core. For example, the nanoparticle core can incorporate or can be loaded with a magnetic core or metal (e.g., iron). For example, the metal can be a transition metal or lanthanide (e.g., Mn, Gd, Co, etc.). As another example, in biological systems, this magnetic core can be iron. As another example, different metals can be used to make recombinant ferritin nanoparticles that are suitable for various imaging applications (e.g., change MR properties), changing toxicity, or thermal ablation therapy. Different magnetic cores or metals may be suitable for different imaging modalities or imaging of different tissues and organs. As another example, the nanoparticle core can comprise a radiolabel.

Inside a natural ferritin shell, iron ions form crystallites together with phosphate and hydroxide ions. The resulting particle is similar to the mineral ferrihydrite. As shown here, the human recombinant ferritin, as described herein, can incorporate a core nanoparticle suitable for radioimaging or magnetic resonance imaging (MRI) applications. In some embodiments, the core nanoparticle can comprise an iron oxide core with a core diameter between about 1 nm and about 8 nm, between about 1 nm and about 5 nm, or between about 1 nm and about 2 nm (the apoferritin core is about 8 nm in diameter, which can limit the size of the core, but can be variable depending on the HC or LCs used). For example, the core nanoparticle can have a core diameter of 20 nm or less, about 15 nm or less, about 10 nm or less, about 5 nm or less, about 4 nm or less, about 3 nm or less, about 2 nm or less, or about 1 nm or less. Recitation of each of these discrete values is understood to include ranges between each value. Recitation of each range is understood to include discrete values within the range.

As another example, the nanoparticle core can be loaded with a radiolabel for positron emission tomography (PET) or other imaging modalities.

For example, the nanoparticle core can comprise a pure metal, such as aluminum, antimony, arsenic, barium, beryllium, bismuth, boron, cadmium, calcium, cerium, cesium, chromium, cobalt, copper, dysprosium, erbium, europium, gadolinium, gallium, germanium, gold, hafnium, holmium, indium, iridium, iron, lanthanum, lead, lithium, lutetium, magnesium, manganese, mercury, molybdenum, neodymium, nickel, niobium, osmium, palladium, platinum, potassium, praseodymium, rhenium, rhodium, rubidium, ruthenium, samarium, scandium, selenium, silicon, silver, strontium, tantalum, tellurium, terbium, thallium, thulium, tin, titanium, tungsten, vanadium, ytterbium, yttrium, zinc, or zirconium.

As another example, the nanoparticle core can comprise a metal compound, such as a metal oxide, a metal alloy, a metal sulfide, a metal halide, a metal chloride, a metal fluoride, a metal phosphate, or a metal hydroxide.

As another example, the nanoparticle core can be a mixed maghemite/magnetite core.

As described herein, the nanoparticle core of the imaging agent can comprise a radiolabeled metal. Radiolabeling processes are well known in the art (see e.g., Fani et al. *Theranostics* 2012; 2(5):481-501). For example, suitable radiolabeled metals can be: $^{72}$As, $^{74}$As, $^{64}$Cu, $^{67}$Cu, $^{68}$Ga, $^{86}$Y, or $^{89}$Zr, among others described herein.

Radiolabel

As described herein, the present disclosure provides for a radiolabeled recombinant ferritin nanoparticle with a magnetic core and/or a radionuclide or radioisotope. The inventors discovered a highly sensitive MRI technique using ferritin filled with iron and then cationized resulting in catonized ferritin (CF). Because the MRI approach requires a larger dose of CF, the inventors also formulated a radioCF. The presently described radioCF formulation can be detected in micro-doses, reducing the potential for toxicity. Measurement of nephron number and single nephron function represents a new paradigm for diagnostics in the kidney, and radioCF can bridge the gap between research tools and clinical application.

The radioisotope can comprise a metal radioisotope complexed with the magnetic core and/or an inner surface of the recombinant apoferritin cage. As described herein, the radioisotope can comprise copper-64 (i.e., Cu-64 or $^{64}$Cu).

In some embodiments, the radioisotope comprises a positron emitting isotope suitable for use in PET imaging. For example, the radioisotope can comprise a synthetic radioisotope. For example, the radioisotope can be a positron emitter selected from $^{14}$O, $^{15}$O, $^{13}$N, $^{11}$C, $^{18}$F, $^{22}$Na, $^{26}$Al, $^{82}$Rb, $^{38}$K, $^{62}$Cu, $^{63}$Zn, $^{70}$As, $^{68}$Ga, $^{61}$Cu, $^{52}$Fe, $^{62}$Zn, $^{63}$Zn, $^{64}$Cu, $^{86}$Y, $^{76}$Br, $^{55}$Co, $^{71}$As, $^{74}$As, $^{68}$Ge, $^{40}$K, $^{121}$I, $^{120}$I, $^{110}$In, $^{94}$Tc, $^{122}$Xe, $^{89}$Zr, or $^{124}$I. In some embodiments, the radioisotope comprises $^{64}$Cu.

As described herein, the radiolabel can be incorporated with the imaging agent by various methods. For example, the radiolabel can be absorbed onto the surface of the magnetic core. As another example, the radiolabel can be chelated and incorporated into the binding site of the apoferritin.

Other examples of suitable, non-limiting radiolabel groups can be: $^2$H (D or deuterium), $^3$H (T or tritium), $^{11}$C, $^{13}$C, $^{14}$C, $^{64}$Cu, $^{67}$Cu, $^{177}$Lu, $^{13}$N, $^{15}$N, $^{15}$O, $^{17}$O, $^{18}$O, $^{18}$F, $^{89}$Sr, $^{35}$S, $^{153}$Sm, $^{36}$Cl, $^{32}$Br, $^{75}$Br, $^{76}$Br, $^{77}$Br, $^{123}$I, $^{124}$I, $^{125}$I, $^{131}$I, $^{111}$In, $^{67}$Ga, $^{68}$Ga, $^{177}$Lu, $^{186}$Re, $^{188}$Re, $^{201}$Tl, $^{99m}$Tc, $^{90}$Y, or $^{89}$Zr. It is to be understood that an isotopically labeled compound needs only to be enriched with a detectable isotope to, or above, the degree which allows detection with a technique suitable for the particular application, e.g., in a detectable compound labeled with $^{11}$C, the carbon-atom of the labeled group of the labeled compound may be constituted by $^{12}$C or other carbon-isotopes in a fraction of the molecules. The radionuclide that is incorporated in the radiolabeled compounds will depend on the specific application of that radiolabeled compound. For example, "heavy" isotope-labeled compounds (e.g., compounds containing deuterons/heavy hydrogen, heavy nitrogen, heavy oxygen, heavy carbon) can be useful for mass spectrometric and NMR based studies. As another example, for in vitro labelling or in competition assays, compounds that incorporate $^3$H, $^{14}$C, or $^{125}$I can be useful. For in vivo imaging applications $^{11}$C, $^{13}$C, $^{18}$F, $^{19}$F, $^{120}$I, $^{123}$I, $^{131}$I, $^{75}$Br, or $^{76}$Br can generally be useful.

References herein to "radiolabeled" include a compound where one or more atoms are replaced or substituted by an atom having an atomic mass or mass number different from the atomic mass or mass number typically found in nature (e.g., naturally occurring). One non-limiting exception is $^{19}$F, which allows detection of a molecule which contains this element without enrichment to a higher degree than what is naturally occurring. Compounds carrying the substituent $^{19}$F may thus also be referred to as "labelled" or the like. The term radiolabeled may be interchangeably used with "isotopically-labelled", "labelled", "isotopic tracer group", "isotopic marker", "isotopic label", "detectable isotope", or "radioligand".

In one embodiment, the compound comprises a plurality of radioisoptoes incorporated into the ferritin-based imaging agent.

Cationic Recombinant Ferritin

As described herein, the contrast or imaging agent can comprise cationic human recombinant ferritin (e.g., functionalized recombinant ferritin), a chemically modified version of a recombinant protein having at least one HC of native human ferritin (or functional variant thereof). The positive charge allows the agent to bind transiently to the glomerular basement membrane in the kidney. With cationization, the ferritin nanoparticle can function as a versatile container for targeted drug delivery or diagnostics. Recently, cationic ferritin (CF) has been developed as a targeted MRI contrast agent to provide quantitative maps of human nephron number and glomerular size in the kidney. After intravenous injection, CF traverses the glomerular basement membrane (GBM) and binds transiently to the constituent anionic proteoglycans.

Cationization refers to the process of treating a substance, such as human recombinant ferritin, with cations to introduce positively charged sites. Cationization processes for ferritin are well known in the art (see e.g., Danon et al. *Journal of Ultrastructure Research* 1972; 38(5-6):500-510). Except as otherwise noted herein, therefore, the process of the present disclosure can be carried out in accordance with such processes.

As an example, cationic ferritin can be produced by first activating the carboxyl groups of ferritin (or the carboxyl group(s) on the heavy chain or light chain of the recombinant ferritin) with a water-soluble carbodiimide (EDC) and subsequently reacting the activated carboxyl groups with a nucleophile, such as N,N-dimethyl-1,3-propanediamine (DMPA) or hexamethyldiamine (HMD). The reactions results in the introduction of tertiary or primary amine groups to the ferritin. Generally, as is well-known in the art, the degree of cationization can be controlled by varying cationization reagents and the pH of the reaction.

Processes for Preparing an Imaging Agent

Described herein are processes for preparing an imaging agent. The process can comprise: complexing a magnetic core and/or a radioisotope with cationic recombinant ferritin comprising a functionalized recombinant ferritin cage and a magnetic core in a reaction mixture to form the imaging agent, wherein the functionalized recombinant ferritin cage comprises a cationic functional group.

As an example, the methods described herein can comprise functionalizing recombinant ferritin with a cationic functional group to form cationic recombinant ferritin. As another example, the methods described herein can comprise complexing a recombinant ferritin with a magnetic core to form the imaging agent. As another example, the recombinant ferritin can be formed by combining apoferritin subunits. As another example, the ferritin can be formed by combining the apoferritin subunits and a magnetic core material.

As described herein, the method can comprise adjusting the pH of the reaction mixture (e.g., adjusting to a pH of about 5 or less). The method can lower the pH to open the cage to open up the ferritin or the recombinant ferritin cage to incorporate a radiolabel. For example, the pH can be adjusted to incorporate a radioisotope within the cationic ferritin subunit, apoferritin subunit, recombinant ferritin, or recombinant apoferritin (e.g., to a pH of about 5). In various embodiments, the method can comprise lowering the pH to incorporate a radioisotope absorbed on a magnetic core surface within the ferritin or recombinant ferritin.

In some embodiments, human ferritin or recombinant ferritin can be purified and cationized.

In some embodiments, human ferritin that isn't a fusion protein or recombinant ferritin can be cationized and radiolabeled.

In various embodiments, the imaging agent formed by the methods described herein can comprise any of the imaging agents or components thereof, described herein.

Imaging Modalities and Detection Methods

The imaging agents, as described herein, can be contrast agents or radioimaging agents suitable for various imaging approaches, such as MRI and/or PET imaging.

As described herein, diagnostic imaging has contributed to improved and early detection of a wide range of pathologies in patients. Imaging is central to preclinical testing and animal models developed for translation. Two key features of diagnostic medical imaging tools are the ability to spatially localize biomarkers without surgical intervention and with potentially higher sensitivity and specificity compared to analysis of biological samples or biofluids.

Magnetic Resonance Imaging (MRI)

Magnetic resonance imaging (MRI), in particular, has received attention because of its outstanding spatial resolution in soft tissue and lack of ionizing radiation, allowing new MRI contrast techniques to be rapidly translated for use in the clinic.

Several radiological imaging approaches have estimated nephron number based on surrogates like cortical or kidney volume. Imaging approaches have been developed to directly measure nephron endowment in vivo using magnetic resonance imaging (MRI) in conjunction with the intravenously injected cationic recombinant ferritin contrast agent. Recombinant ferritin, comprising iron-oxide, can provide high biocompatibility. Intravenously injected recombinant cationic ferritin binds to the glomerular basement membrane and temporarily provides image contrast between the glomeruli and the surrounding tissue in 3D gradient-recalled echo images. Individual glomeruli are then identified from the images using software, and individual glomerular volumes can be mapped in space.

Importantly, cationized ferritin enhanced-MRI (CFE-MRI) can be combined with other acquisition pulse sequences to provide a high-resolution, integrated view of vascular, glomerular, and potentially tubulointerstitial morphology. This combined approach has the potential to inform a new class of studies in the kidney that explore spatiotemporal changes in tissue microstructure and physiology during development of disease and in new therapies. Importantly, CFE-MRI can provide for the measurement of nephron number as a clinical marker of renal health in patients at risk for CKD and in transplant recipients.

One of the potential difficulties of traditional CFE-MRI (e.g., using natural apoferritin as the cage) in clinical translation is the relatively high dose of the current formulation of CF required to overcome detection limits of MRI. Most studies have used the contrast agent in doses of approximately 5 mg/100 g body weight in rodents and in donor human organs, though there are several techniques that allow for detection in approximately 10-100 fold lower doses, but these techniques so far report low yields during synthesis. The driving factor limiting detection of CF with MRI is the relaxivity of the agent, and this can be improved by increasing iron deposition in the core or modifying the chemical makeup of the particles. In addition, custom hardware and software can be integrated with clinical imaging systems. Given the current detectable doses of CFE-MRI, the roadmap toward potential translation to clinical use seems to be through cautious testing in preclinical models in conjunction with regulatory agencies.

MRI contrast agents, by comparison, are typically delivered in higher doses, resulting in toxicity to the patient that may not be immediately observed. This is illustrated by the development of nephrogenic systemic fibrosis in patients with chronic kidney disease who were exposed to linear chelates of gadolinium. Significant efforts focus on reducing the potential toxicity of exogenous agents through chemical modification, using biologically inert materials or "natural" nanomaterials as contrast agents. Accordingly, the present disclosure provides for new imaging agents that can be used both for MRI and lower dose image modalities such as PET.

Positron Emission Tomography (PET)

High-resolution imaging can reveal new microstructural and physiologic features that guide an understanding of heterogeneous disease and responses to therapies. With the current focus on tailoring therapies to individual patients, there is also a need for diagnostic tools that report on pathology at the cellular and molecular level. This typically involves a combination of exogenous contrast agents and radiological imaging. Several radiological imaging modalities, including positron emission tomography (PET), rely completely on exogenous agents for signal. For PET, radioimaging agents are often highly translatable because positron emission is detected in trace doses, allowing for limited toxicity and rapid regulatory approval.

One aspect of the present disclosure provides for a method of detection of a recombinant cationic ferritin contrast agent or imaging agent in a subject. The method of detection can employ any number of imaging modalities known in the art. The specific imaging modality will depend on the target tissue or organ in the subject for which the method of detection is being is used. For example, the method of detection can employ MRI to detect the contrast agent. As another example, the method of detection can employ PET or PET-MRI to detect the contrast or imaging agent. As another example, the method of detection can employ single-photon emission computed tomography (SPECT) to detect the contrast or imaging agent.

Methods of Use

In various embodiments, the imaging agents described herein may be used to image a target in a subject in need thereof. In general, the method for imaging a target in a subject comprises administering the imaging agent to the subject and imaging the target using magnetic resonance imaging (MRI) and/or positron emission tomography (PET). Advantageously, the imaging agents provided herein can be used for both MRI and PET imaging.

Accordingly, in various embodiments, a method of imaging a target in a subject is provided, the method comprises administering the imaging agent provided above, or prepared as described above, to the subject and imaging the target using magnetic resonance imaging (MRI). In various embodiments, the method can comprise imaging the target using positron emission tomography (PET).

A method of imaging a target in a subject is provided herein, the method can comprise administering the imaging agent provided herein, or prepared as described herein, to the subject, and imaging the target. For example, the target can be imaged using magnetic resonance imaging. As another example, the method can comprise imaging the target using positron emission tomography (PET).

Targets for Imaging

Suitable targets for imaging using the imaging agents provided herein include an organ or organ system in a mammal, such as humans. For example, the target can comprise a kidney or kidney cell. Representative cells that may be imaged using this agent can include nephrons or renal glomeruli.

Renal Disease Detection

As described herein, the development of a human recombinant cationic ferritin (HrCF) imaging agent is an important step toward noninvasive determination of nephron endowment in patients with or at risk for chronic kidney disease and may improve transplant matching and monitoring in donors and recipients, human allograft evaluation, and potentially in vivo assessment of renal pathology.

Chronic kidney disease (CKD) is a progressive disease that often ends in renal failure, requiring dialysis or transplant. Current clinical measures to detect renal function in CKD, such as serum or urinary markers, are indirect and insensitive to early development of the disease. Recently, cationic ferritin-enhanced MRI (CFE-MRI) has been developed to detect early microstructural changes by enabling measurements of nephron endowment in rodents and in human organs. CF binds to the glomerular basement membrane after intravenous injection, causing a detectable decrease in T2 at the site of each glomerulus (which can produce contrast in an MRI image).

As described herein, the synthesis and application of a human recombinant form of cationic ferritin (HrCF) was investigated as an iron-oxide nanoparticle imaging agent for renal imaging. A general approach was developed to form an iron oxide core in the recombinant ferritin molecule (fusion protein) in bacteria, allowing for rapid synthesis of a functional agent. For clinical translation, HrCF may overcome limitations in agent compatibility as it is based off of an endogenous protein regularly present in systemic circulation and in cells (ferritin). This study describes a novel, human-based, targeted natural nanoparticle imaging agent for quantitative renal imaging.

After intravenous injection, cationic recombinant ferritin traverses the glomerular basement membrane (GBM) in the kidney and binds transiently to the constituent anionic proteoglycans. With sufficient cationic recombinant ferritin accumulation in the GBM, individual glomeruli can be detected and measured using MRI (see e.g., Example 1 and Example 2) and image segmentation to determine a subject's nephron endowment (e.g., number of glomeruli). Furthermore, measurements of nephron endowment can allow for observation of early, disease-indicating microstructural changes that may not be detected by other diagnostic methods.

Kidney glomerular number and size are strongly linked to renal and cardiovascular health and knowing nephron endowment enables new investigations into development of chronic kidney disease, developmental impacts of acute kidney injury, and transplant viability. The ability to detect nephron endowment in vivo would allow for the investigation of the development of chronic kidney disease, impact of acute kidney injury, viability of a renal allograft, and a novel metric to assess the renal toxicity of new drugs. Previous applications of CF have been based on commercial horse spleen ferritin, which is readily available and modified for CFE-MRI in a range of animals and ex vivo human tissues. To date, limited toxicity of the horse derived CF has been observed, which was abrogated by administration of single dose of hydrocortisone prior to administration of the CF. But previous work has demonstrated that repeated high doses of a targeted foreign protein can be used to produce focal immune complex deposition as a model for autoimmune disease. Described herein is a cautious approach to developing a glomerulus-targeted contrast agent such as CF. With the goal of translating this technology for use in viable human tissue or in vivo for clinical use, it was sought to create a form of CF that would naturally mimic the ferritin normally present in human circulation and in human cells.

One aspect of the present disclosure provides for methods of assessing renal pathology or renal function in a subject having or suspected of having a renal pathology, disease, or disorder. For example, a renal pathology, disease, or disorder can be Alagille syndrome, Alport syndrome, amyloidosis, chronic kidney disease (CKD), cystinosis, diabetic neuropathy (DN), end-stage renal disease (ESRD), Fabry disease, focal segmental glomerulosclerosis, glomerulonephritis, Goodpasture syndrome, atypical hemolytic uremic syndrome (aHUS), hemolytic uremic syndrome (HUS), Henoch-Schonlein purpura, hypertensive kidney disease, IgA nephropathy (Berger's disease), interstitial nephritis, kidney cancer, lupus nephritis, minimal change disease, nephropenia, nephrotic syndrome, polycystic kidney disease (PKD), renal cell carcinoma, renal sarcoma, renal vascular disease, thrombotic thrombocytopenic purpura (TTP), granulomatosis with polyangiitis (GPA), transitional cell carcinoma, urothelial cell carcinoma, or Wilms tumor.

One embodiment of the present disclosure provides for methods of assessing renal pathology or renal function in a subject suffering from chronic kidney disease (CKD). CKD is a progressive disease that often ends in renal failure, requiring dialysis or transplant. Current clinical measures to detect renal function in CKD, such as serum or urinary markers, are indirect and insensitive to early development of the disease. Recently, cationic ferritin-enhanced MRI (CFE-MRI) has been developed to detect early microstructural changes by enabling measurements of nephron endowment in rodents and in human organs. Cationic ferritin binds to the glomerular basement membrane after intravenous injection, causing a detectable decrease in T2 (which provides increased MRI contrast) at the site of each glomerulus. Recombinant ferritin is used herein as an extension of CFE-MRI. CFE-MRI was coined to describe the quantitative imaging performed using cationic ferritin (previously horse spleen derived). Here is described methods and compositions for CFE-MRI using recombinant human cationic ferritin.

Transgenic Microorganism

One aspect of the present disclosure provides for a transgenic microorganism capable of accumulating an assembled human recombinant ferritin protein product. As described herein, human heavy chain (HC) and light chain (LC) ferritin can be recombinantly co-expressed such that the ferritin spontaneously assembles and incorporates iron within E. coli (see e.g., Example 1, Example 2, Example 5). Once purified, the expressed human recombinant protein can be cationized to form human recombinant cationic ferritin (HrCF) and used as a flexible contrast agent with MRI or other imaging modalities.

The advantage of HrCF is immunologic reactions during application in human imaging will be minimized. Inducing the formation of the iron oxide crystal (or particle) in situ helps to maintain a high synthesis yield. The incorporation of iron in situ simplifies the formation of an iron oxide nanoparticle in the core, maintaining a high synthesis yield and reducing the amount of post-purification modifications required to form it.

As described herein, a transgenic microorganism can be any microorganism capable of recombinant expression of assembled human ferritin protein. For example, a transgenic microorganism can be a bacterium, a yeast, an algae, or a mammalian cell. For example, the transgenic microorganism is an *E. coli* bacterium.

As described herein, human ferritin heavy chain (HC) and human ferritin light chain (LC) cDNA can be cloned into a vector (e.g., pVEXK-HN vector) for expression of ferritin. The vector can incorporate a His tag at the N-terminus of the heavy chain suitable for ready purification of the recombinant ferritin via affinity chromatography. Any number of expression vectors may be used, expression vectors and methods of selecting suitable expression vectors are well known in the art (see e.g., Rosano and Ceccarelli (2014) Recombinant Protein Expression in Microbial Systems, Frontiers E-Books, ISBN-10: 978-2-88919-294-6).

As described herein, heavy and light chain ferritin DNA segments were separated by an Internal Ribosome Entry Site (IRES) to allow for the co-expression of both ferritin chains (e.g., a bicistronic sequence). An IRES can be any polynucleotide sequence that allows for translation initiation of a target transcript in manner that is independent of the 5' cap structure, which is generally found at the 5' end of an mRNA transcript. In a bicistronic sequence, the IRES sequence drives translation of the second, downstream protein coding sequence independently of the 5' cap structure, allowing both the upstream and downstream sequences to be transcribed. Efficient IRES sequences are determined through routine experimentation with methods well-known in the art. For example, an IRES sequence can be an IRES derived from a viral genome, such as a Picornavirus, Aphthovirus, Kaposi's sarcoma-associated herpesvirus, Hepatitis A, Hepatitis C, Pestivirus, Cripavirus, or *Rhopalosiphum padi* virus. As another example, an IRES sequence can be derived from a cellular mRNA, such as FGF-1, FGF-2, PDGF, VEGF, IGF-II, Antennapedia, Ultrabithorax, MYT-2, NF-KB repressing factor NRF, AML/RUNX1, Gtx homeodomain protein, (eIF4G)a, (eIF4GI)a, EIF4G2, DAP5, c-myc, L-myc, Pim-1, protein kinase p58PITSLRE, p53, SLC7A1, Cat-1, nuclear form of Notch 2, voltage gated potassium channel, Apaf-1, XIAP, HIAP2, Bcl-xL, Bcl-2, ARC, alpha subunit of calcium calmodulin dependent kinase II dendrin, Map2, RC3, amyloid precursor protein, BiP, heat shock protein 70, beta subunit of mitochondrial H+ ATP synthase, ornithine decarboxylase, connexins 32 and 43, HIF-1 alpha, orAPC.

As described herein, constitutive expression of recombinant human ferritin can be induced in a culture of *E. coli* (e.g., with 1 mM Isopropyl-13-D-thio-galactoside (IPTG)). Methods of inducing expression in a transgenic microorganism are well known in the art. As such, any suitable induction method can be used. An iron containing composition (e.g., ferrous citrate) can be added to the culture in order to allow for the incorporation iron into the core of the ferritin protein. Any iron containing composition known in the art suitable for forming a core comprising iron can be used. The recombinant human ferritin was then purified by affinity chromatography and size exclusion chromatography. After lysis and purification, the recombinant ferritin expressed under varying levels of iron in the medium were highly soluble and stable in solution (see e.g., FIG. 1).

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling or cloning. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position+1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A construct of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m=81.5°$ C.$+16.6(\log_{10}[Na^+])+0.41$ (fraction G/C content)$-0.63$(% formamide)$-(600/l)$. Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

| Conservative Substitutions I | |
|---|---|
| Side Chain Characteristic | Amino Acid |
| Aliphatic Non-polar | G A P I L V |
| Polar-uncharged | C S T M N Q |
| Polar-charged | D E K R |
| Aromatic | H F W Y |
| Other | N Q D E |

| Conservative Substitutions II | |
|---|---|
| Side Chain Characteristic | Amino Acid |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

| Conservative Substitutions III | |
|---|---|
| Original Residue | Exemplary Substitution |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met(M) | Leu, Phe, Ile |
| Phe (F) | Leu, Val, Ile, Ala |
| Pro (P) | Gly |
| Ser (S) | Thr |
| Thr (T) | Ser |
| Trp(W) | Tyr, Phe |
| Tyr (Y) | Trp, Phe, Tur, Ser |
| Val (V) | Ile, Leu, Met, Phe, Ala |

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides (ASOs), protein aptamers, nucleotide aptamers, and RNA interference (RNAi) (e.g., small interfering RNAs (siRNA), short hairpin RNA (shRNA), and micro RNAs (miRNA) (see e.g., Rinaldi and Wood (2017) Nature Reviews Neurology 14, describing ASO therapies; Fanning and Symonds (2006) Handb Exp Pharmacol. 173, 289-303G, describing hammerhead ribozymes and small hairpin RNA; Helene, et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc., Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, intradermal, intratumoral, implanted, intramuscular, intraperitoneal, intravenous, intrathecal, intracranial, intracerebroventricular, subcutaneous, intranasal, epidural, intrathecal, ophthalmic, transdermal, or buccal.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to vectors, cells, recombinant ferritin protein, recombinant ferritin protein subunits or recombinant ferritin protein cDNA, cell media, a magnetic core component, a radiolabel, a metal, or a metal solution. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium or video. Detailed instructions may not be physically associated with the kit, instead, a user may be directed to an Internet web site specified by the manufacturer or distributor of the kit.

A control or a reference as described herein can be human ferritin, human apoferritin, or human recombinant apoferritin. A reference value can be used in place of a control or reference sample, which was previously obtained. A control or a reference can also be a sample with a known amount of a detectable compound or a spiked sample.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Recombinant Expression and Synthesis of a Targeted Human Contrast Agent for Quantitative Renal MRI This example describes the synthesis and use of human recombinant cationic ferritin (HrCF) fusion protein for renal MRI imaging. Here is described the synthesis and use of a human recombinant cationic ferritin nanoparticle, synthesized in *E. coli*, as a contrast agent for targeted renal MR imaging. Injected nanoparticles accumulated in the glomerular basement membrane in a mouse, allowing measurement of nephron endowment using gradient echo imaging and automated segmentation. Use of human recombinant contrast agents may allow improved biocompatibility for clinical translation. See, also, Example 2 for additional details.

Methods

Human ferritin heavy chain (HC) and human ferritin light chain (LC) cDNA was cloned into the pVEXK-HN expression vector with a His tag at the N-term of the heavy chain (pVEXK—HN-HC-IRES-LC, Nature Technology Corporation). Protein was expressed using the host strain BL21 (DE3) (New England Biolabs) in LB broth (Luria-Bertani broth, BD) at 37° C. Expression was induced at an OD600 of 0.5 with 1 mM Isopropyl-13-D-thio-galactoside (IPTG, Gold Biotechnology) after adding ferric ammonium citrate (2 mM) and cells were harvested after 24 h. Recombinant human ferritin was purified by a two-step process: 1) affinity chromatography (HisPur cobalt, ThermoFisher) and 2) size exclusion chromatography (HiPrep 16/60 Sephacryl S-200, GE Healthcare). Ferritin formation and iron core was confirmed using transmission electron microscopy (TEM, Hitachi HT7700). HrCF was cationized by a previously published method. To verify detection with MRI, HrCF was injected intravenously (IV) into a male B6 mouse at 5.75 mg per 100 g, and the kidneys were removed and imaged in glutaraldehyde on a 7 T Agilent scanner with a 3D GRE pulse sequence (TE/TR=30/80 ms, 40×40×60 µm resolution). Glomeruli were segmented in the images and counted using in Matlab. (Mathworks).

Results

Transformed bacteria produced human recombinant ferritin which was aqueous in solution after purification. Darkness varied by iron added to bacterial culture during synthesis (see e.g., FIG. 1A). The ferritin formed a 13 nm 24mer nanoparticle with 5 nm iron oxide core as confirmed by SDS-PAGE and TEM (see e.g., FIG. 1B-FIG. 1C). HrCF was detected after intravenous injection by GRE-MRI in perfused, fixed mouse kidneys. Glomerular labeling was visible as small punctate dots in the MRI, and dots were not present in unlabeled control (see e.g., FIG. 3). Glomeruli were identified by custom software. Nephron number in the mouse kidney ($N_{glom}$=18,186), was consistent with previous reports.

DISCUSSION

This study demonstrates the synthesis and use of a human recombinant ferritin nanoparticle as contrast agent for targeted renal imaging. HrCF was used to label the glomeruli after intravenous injection to calculate nephron endowment. HrCF could be critical to translating this technology to measure nephron endowment for human allograft evaluation and potentially in vivo assessment of renal pathology.

Example 2: Recombinant Expression and Self-Assembly of Iron-Loaded Human Ferritin as a Targeted Mri Contrast Agent for Renal Imaging This example describes how human recombinant ferritin comprising both heavy and light chains can be expressed and form a nanoparticle complex with iron in bacteria, purified, and catonized to form a targeted MRI contrast agent for renal imaging.

Herein is a report describing constitutive recombinant expression of human heavy chain and light chain ferritin that spontaneously assembles and incorporates iron within *E. coli*. Once purified, the expressed human recombinant protein can be cationized to form human recombinant cationic ferritin (HrCF) and used as a flexible contrast agent with MRI. The development of HrCF is an important step toward noninvasive determination of nephron endowment in patients with or at risk for chronic kidney disease and may improve transplant matching and monitoring in donors and recipients.

Results

Human Recombinant MRI Contrast Agent Expression in *E. coli*

Figure 2:
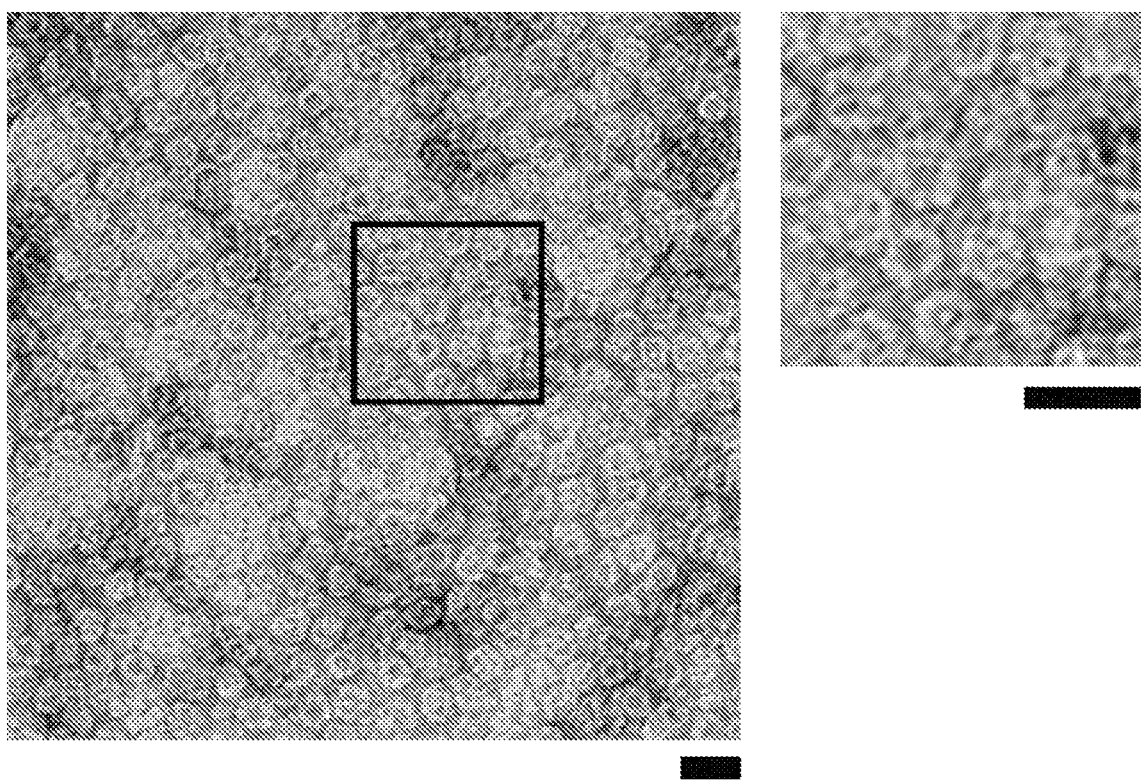
FIG. 2 is a transmission electron microscopy (TEM) image confirming fully formed recombinant human ferritin in the purified eluents after expression in *E. coli*. Holoferritin molecules were spherical and ~13 nm in outer diameter with a core of ~8 nm. In many cases the pores in the outer shell were visible. The core contained variable amounts of iron loading indicated by high electron density in the center. Right image is an enlargement of the box in the image at left. Scale bars=20 nm.

H- and L-ferritin were co-expressed in *E. coli* grown in ferric ammonium citrate in concentrations ranging from 50 µM to 20 mM to the growth medium. After induced expression, lysis, and purification, the ferritin was highly soluble and stable in solution, as shown in FIG. 1A. There was no visible precipitation and samples formed under varying concentrations of iron varied in darkness under brightfield (see e.g., FIG. 1A). Iron incorporation was highest in the ferritin purified from the *E. coli* grown in 2 mM of an iron loading agent (here, ferric ammonium citrate was used), which was used for imaging experiments. The size of purified holoferritin was confirmed by size exclusion chromatography (see e.g., FIG. 1B). Synthesis and purification steps were repeated six times with similar results. The expression of both H- and L-subunits was confirmed by polyacrylamide gel electrophoresis (see e.g., FIG. 1C-FIG. 1D) for ten batches each of *E. coli* grown. Electron microscopy of the purified sample revealed complete formation of the spherical ferritin molecules, with iron incorporation in the core confirmed by electron density (see e.g., FIG. 2).

Iron incorporation in the core was confirmed using inductively coupled plasma mass spectrometry (ICP-MS), where ~250 iron atoms per ferritin molecule was observed compared to no iron in apoferritin and ~1500 iron atoms per molecule in commercial horse spleen ferritin. Transmission electron microscopy (TEM) of adsorbed samples stained with uranyl acetate revealed spherical ferritin nanoparticles of 13 nm diameter with a core and visible pores in the surface, as expected of human ferritin (see e.g., FIG. 3A-FIG. 3B). Iron incorporation in the core was visible due to high electron density, but less fully incorporated compared to commercial horse spleen ferritin as predicted by ICP-MS.

Dynamic light scattering (DLS) was performed to confirm the size of the HrCF molecule after expression compared to horse spleen ferritin. The sizes were very similar, at ~13 nm on average in recombinant and horse spleen (see e.g., FIG. 3C).

Magnetic Resonance Imaging of HrCF after Intravenous Injection in Mice

To confirm that HrCF performs as a viable MRI contrast agent, CFE-MRI was performed using HrCF, using protocols developed in previous studies using commercial horse spleen ferritin.

Figures 3A, 3B, 3C, 3D, 3E, 3F:
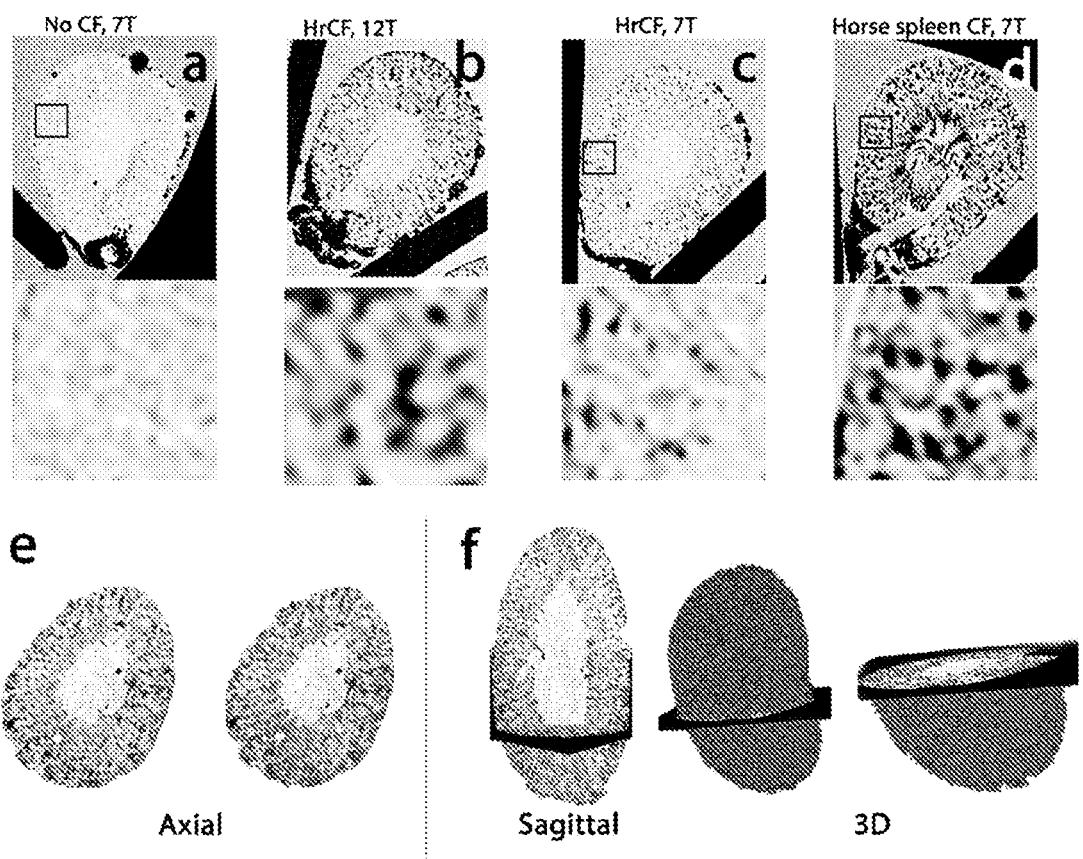
FIG. 3A-FIG. 3F is a series of magnetic resonance imaging (MRI) images of intravenously injected HrCF to allow for the identification of individual renal glomeruli by MRI. MRI (axial slices from 3D gradient-recalled echo datasets) in perfused, fixed mouse kidneys with and without in vivo intravenous injection of HrCF at two magnetic field strengths. (A) Kidneys of mice that did not receive HrCF, showing no glomerular labeling at 12 T. (B) Glomerular labeling by intravenously injected HrCF was evident in the cortex in 3D MRI as punctate dark spots at 12 T and (C) at 7 T. Glomerular labeling by HrCF was less intense at 7 T than for commercial horse spleen cationic ferritin (D) due to less iron incorporation during bacterial synthesis. (E) Glomeruli were automatically detected by image processing and (F) rendered in 3D to map the spatial distribution of nephrons throughout the kidney.

Once the structure and iron content of the human recombinant ferritin was confirmed, the molecule was cationized by the addition of surface amine groups that would cause it to bind to the glomerular basement membrane after intravenous administration. CFE-MRI was performed on excised, perfused kidneys of mice with or without injected HrCF in an MRI with a magnetic field strength of 12 T. As seen in FIG. 3A-FIG. 3B, the kidneys from mice labeled with HrCF had dark, punctate spots in the gradient-echo MR images in the cortex confirming the binding of the HrCF to the GBM and consistent with previous observations using horse spleen CF. Un-injected controls had no spots (see e.g., FIG. 3A), also consistent with the previous observations using horse spleen CF. Next, it was confirmed that HrCF can also be detected at the lower, more common and clinically used field strength of 7 T, since there was reduced iron content observed by ICP-MS. As seen in FIG. 3C-FIG. 3D, the HrCF was detected in the glomeruli with reduced signal intenisty compared to 12 T. Glomerular signals were also less intense than observed with commercial horse spleen-derived ferritin. Measured glomerular number ($N_{glom}$) was 12,899±263 in kidneys imaged by HrCFE-MRI at 12 T, compared to 13,410±129 measured at 7 T in the same kidneys. This difference was within the measured error created by false positive detection of 2155 (15%) at 12 T. $N_{glom}$ was also consistent with previously measured $N_{glom}$ in this strain from stereology and MRI.

DISCUSSION

Here, the recombinant expression and iron loading of human recombinant H-L ferritin in *E. coli* and the functionalized HrCF can be used as a targeted contrast agent for quantitative renal imaging has been demonstrated. The injected HrCF allows each functioning nephron in the kidney to be identified, providing a new direct biomarker of renal health. The use of HrCF overcomes limitations of commercially derived products because it can be produced under controlled manufacturing conditions aimed at use in the clinic. HrCF thus represents a critical step toward direct measurement of nephron endowment or glomerular number in humans.

Previous work has demonstrated that apoferritin can serve as a versatile nanocarrier to deliver diagnostic or other agents. In fact, the use of ferritin has been recently recommended as a potential platform for a range of clinically translatable diagnostic and therapeutic tools. The hollow core of the ferritin molecule can serve as a container and, importantly, can enable controlled deposition of metal oxides or ions. The protein shell of ferritin makes it readily functionalizable, as demonstrated here by cationization for the purposed of targeted molecular imaging by MRI. Translation of HrCF will be achieved by demonstrating synthesis under protocols designed to eliminate batch variability, and through continued demonstrations of efficacy and safety in human and animal tissues.

One key feature of HrCF is that it requires minimal modification after expression and purification due to the direct use of the *E. coli* iron trafficking using ferric citrate transporters. This increases yield over benchtop synthesis and reduces the time to form the contrast agent. Future work will focus on optimizing iron uptake in *E. coli*.

Animal Protocol

The Institutional Animal Care and Use Committee at the University of Virginia approved all experiments. A wild type (WT), C57BL6/N, mouse (n=1) received HrCF intravenously over 4 injections separated by 90-minute intervals. Ninety minutes after the final injection, mice were perfused trans-cardially with saline followed by formalin and kidneys were resected and stored in 2% glutaraldehyde in 0.1 M cacodylate for ex vivo MRI. Numerous reports have shown the specific binding of cationic horse spleen ferritin (CF) to glomeruli in perfused kidneys as well as the lack of contrast enhancement in perfused kidneys without CF. Thus, a single WT mouse that received 5.75 mg/100 g-body-weight of CF intravenously over 2 injections (Sigma) was used to reconfirm contrast enhancement in the kidney cortex and a single un-injected WT mouse was used for a negative control.

Materials and Methods

Contrast Agent Synthesis and Purification

Human ferritin heavy chain (HC) and human ferritin light chain (LC) cDNAs were purchased from Origene. To make a dual cistron vector, the HC was cloned into pVEXK HN downstream of the HN tag using NdeI-SalI. Then the human ferritin light chain was cloned downstream as a SalI-EcoR1 fragment. The cistronic ribosomal binding site from ZWF-ripA was included between the genes. The encoded heavy chain was therefore polyhistidine tagged, but the light chain was not. Primers for polymerase chain reaction from the Origine construct for H-chain were gacaagcatatgacgaccgcgtccacctcgcag (SEQ ID NO: 1) and gcctccgtcgacttagctttcattatcactgtctcccag (SEQ ID NO: 2). Primers for L-chain were gcctcagtcgacgaggagataacatat-gagctcccagattcgtcagaattattccac (SEQ ID NO: 3) and cacgat-gaattcttattagtcgtgcttgagagtgagcctttcg (SEQ ID NO: 4). Cloning was confirmed using digestion, gel purification of several fragments, and sequencing of the pVEX2'HC sequence. BL21 bacteria were transformed and plated with LBK and glucose. Expression was tested first in iron free minimal media. Once expression was confirmed, 2 mg of the protein was purified from a 1 L medium for initial testing.

Human Ferritin Expression and Purification

The construct was transformed into BL21 (DE3) cells (New England Biolabs) for recombinant protein expression.

LB broth (Luria-Bertani broth, BD) was inoculated with an overnight culture (1/40) at and cultured at 37° C. and 250 rpm until OD600 reached ~0.5. At this time, ferric ammonium citrate was added to the final concentration of up to 2 mM and recombinant protein expression was induced with 1 mM Isopropyl-β-D-thio-galactoside (IPTG, Gold Biotechnology). Culture was induced for 24 h at 37° C. and 250 rpm. Cells were harvested after 24 h induction, pelleted (30 min at 8000 rpm and 4° C.) and re-suspended in: 50 mM Tris pH 8.0, 300 mM NaCl and 5 mM imidazole. BugBuster (1×, EMD Millipore), $MgCl_2$ (0.5 mM), PMSF (100 mM, Gold Biotechnology) and DNAse (0.5 µg/mL) were added for cell lysis and cell suspension was mixed by rotation for 20 min at room temperature. Cell lysate was spun for 30 minutes at 18500 rpm at 4° C. The cleared lysate was then applied to a HisPur cobalt column (ThermoFisher Scientific) equilibrated with 50 mM Tris pH 8.0, 300 mM NaCl and 5 mM imidazole. The column was washed before eluting the protein off the column with 50 mM Tris pH 8.0, 300 mM NaCl and 500 mM imidazole. For characterization, 20 µL samples were taken and loaded in a 12.5% SDS page gel (200 V for 45 min) along with 7 µL of Biorad protein standard. Protein was further purified by size exclusion chromatography on a HiPrep 16/60 Sephacryl S-200 HR column (GE healthcare Life Sciences). Following size exclusion chromatography, protein was concentrated using a filter membrane (INFO) for 10 minutes at 4800 rpm and 4° C. Protein concentration was measured with a Biorad DC assay. All components were purchased from Sigma unless otherwise stated.

Characterization

Recombinant ferritin formation and iron core was confirmed using transmission electron microscopy (TEM, Hitachi HT7700). HrCF was cationized by previously published methods.

Iron Loading in HrCF

Final product of HrCF was analyzed using inductively coupled plasma mass spectroscopy (ICP-MS) to confirm the presence of iron. Prior to sample analysis, external calibration standards of iron (Fe) were measured using 1 µg/L, 10 µg/L, 100 µg/L and 200 µg/L. All measurements of calibration standards were within 10% of expected concentrations, and relative standard deviations were less than 5% for all standards and samples. Acid digestion of samples was performed in preparation for inductively coupled plasma mass spectrometry (ICP-MS). ICP-MS was performed with HrCF, native horse spleen ferritin (Sigma, MO, USA) for positive control, and apoferritin (Sigma) for negative control. First, all samples were prepared to a concentration of 1 mg/mL for acid digestion and analysis. Next, 0.5 mL of samples were placed in Teflon vessels and 1 ml of concentrated nitric acid was added. Samples were then placed into a Mars 6 Microwave Digestion System (CEM Corporation, NC, USA). Microwave power was ramped up to 180° C. over 20 minutes and then held at 180° C. for 20 minutes. After digestion, 8.5 mL of $dH_2O$ was added to digestion mixture. Next, 9.9 mL of $dH_2O$ was added to 0.1 mL of the diluted digestion mixture for final analysis. Preparation, digestion and analysis was repeated twice for each original sample. In one sample from the positive control, 0.05 mL of sample solution in 9.95 mL of $dH_2O$ was added due to a higher than expected calibration curve in the first dilution.

Transmission Electron Microscopy (TEM)

Transmission electron microscopy (TEM) was used to view the structure of final HrCF product. TEM of HrCF was compared with TEM of native horse spleen ferritin. Briefly, samples were loaded on a 200-mesh carbon coated plus Formvar-coated copper grid (Ted Pella, Inc., CA, USA) and negatively stained with ~1% uranyl acetate. Stained grids with sample were viewed on a Hitachi (Chiyoda, Tokyo, Japan) HT7700 TEM at 100 kV, at a magnification of ×100, and photographed with an Advanced Microscopy Techniques (Advanced Microscopy Techniques, Corp, MA, USA) XR-41 B 2k×2k CCD camera.

Ferritin Size Measurements

Average protein size was also characterized using dynamic light scattering (DLS). Briefly, all samples were prepared to an initial concentration of 1 mg/mL and then directly measured with a Malvern ZEN3600 DLS (Malvern Instruments, Worcestershire, United Kingdom). Size measurements of HrCF was compared with native horse spleen ferritin and apoferritin.

Magnetic Resonance Imaging (MRI) and Microscopy

The Institutional Animal Care and Use Committee at the University of Virginia approved all experiments. Two C57BL6/N mice received HrCF intravenously over 4 injections separated by 90-minute intervals. Ninety minutes after the final injection, mice were perfused trans-cardiacally with 0.9% sodium chloride followed by formalin. Kidneys were resected and stored in 2% glutaraldehyde in 0.1 M cacodylate for ex vivo MRI. An un-injected WT mouse for a negative control.

To verify detection with MRI, HrCF was injected intravenously into two male C57B1/B6 mice at 5.75 mg per 100 g.

The total dose was delivered over four injections separated by 90 minutes. The animals were transcardially perfused under anesthesia 90 minutes after the last injection. Kidneys were removed and placed in 2% glutaraldehyde in 0.1 M cacodylate.

Kidneys were imaged together using an Agilent 11.74 T DirectDrive MRI (Agilent, CA, USA) and using a 3D GRE pulse sequence with the following parameters: TE/TR=25/100, resolution=52.7×52.7×58.6 $\mu m^3$, flip angle (a)=30°. To compare the images with work at lower field (7 T) using commercial horse spleen CF (Sigma), kidneys were also imaged using a Bruker 7 T/30 MRI (Bruker, Co., MA, USA), and a 3D gradient recalled echo (GRE) pulse sequence with the following parameters: TE/TR=30/100, resolution=42.2×42.2×60 $\mu m^3$, α=30°.

Glomerular number ($N_{glom}$) was measured from the 3D MRI of CF-labeled kidneys using MIPAR (Worthington, OH, USA). The process is as follows. 1) The image was resampled by 4 using Lanczos resampling. 2) To create an initial mask, the contrast was adjusted and enhanced the image brightness. By using basic threshold all the white pixels were selected to separate images from their background and from large holes. 3) Adaptive thresholding was applied to the first mask and the second mask was created to identify dark punctate spots using second mask. 4) Objects less than 4 pixels were removed. 5) The connected features were separated using watershed algorithm and the outcome was labeled as a glomerulus. Finally, Amira software (Thermo Fisher Scientific, Waltham, MA) was used for 3D rendering and visualization.

Example 3: Contrast Agents to Measure Kidney Nephron Endowment Using Positron Emission Tomography (PET)

This example describes an imaging agent or a contrast agent based on apoferritin, with or without iron in the core loaded with Copper-64 and functionalized on its surface to confer a positive charge. The positive charge allows the agent to bind transiently to the glomerular basement membrane in the kidney. The product is called "radioCF". The binding of radioCF to the glomerular basement membrane can be used in conjunction with PET to determine whole kidney nephron endowment.

Nephron loss is a primary feature of chronic kidney disease that affects approximately 15% of the world population, including in the USA. Current techniques to monitor nephron number in humans are inaccurate or destructive (e.g., serum creatinine or biopsy). The inventors developed a highly sensitive MRI technique using apoferritin filled with iron and cationized ferritin (CF). However, the MRI approach requires a larger dose of CF that PET would require. The current radioCF formulation can be detected in micro-doses, reducing the potential for toxicity and making it likely to be readily translated for use in live human patients. Measurement of nephron number and single nephron function represents a new paradigm for diagnostics in the kidney, and radioCF can bridge the gap between research tools and clinical application.

Synthesis of a radioCF Imaging Agent

Methods

Figure 4:
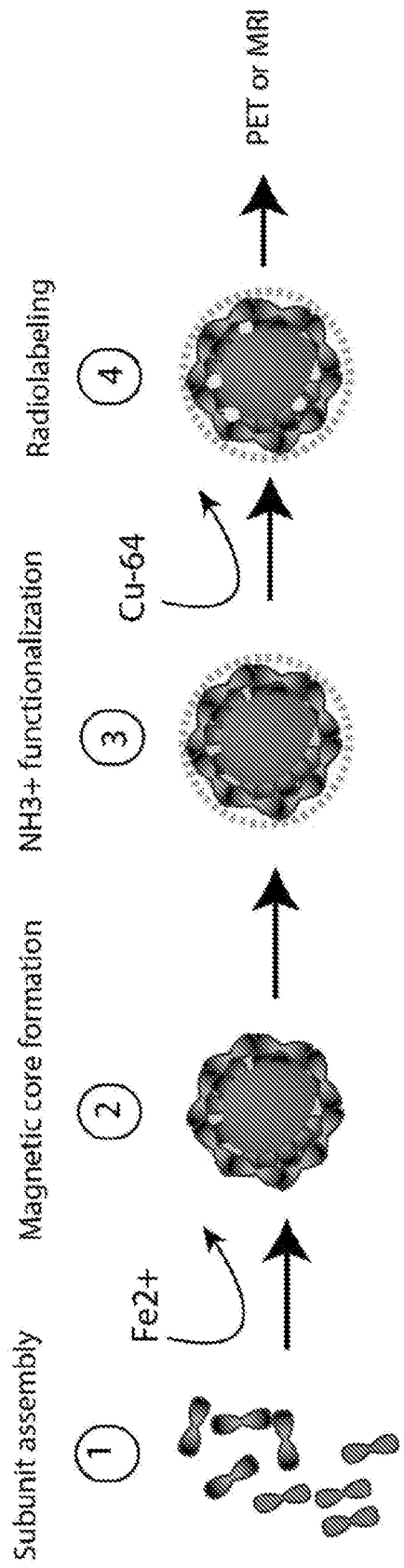
FIG. 4 depicts an illustration of RadioCF synthesis for use as renal glomerulus-targeted contrast agent for PET or MRI. Here, the figure depicts an iron core, but the iron core is optional. 1) Apoferritin subunits are self-assembled in cells or in solution. Iron can be added 2) to form an iron oxide nanoparticle within the ferritin core. 3) Amines are conjugated to the surface to provide a cationic charge to bind to the glomerular basement membrane. Cu-64 is added in a final step 4) to form RadioCF, used in PET or MRI as a marker for nephron endowment and glomerular filtration.

FIG. 4 illustrates the concept of radioCF synthesis, starting with apoferritin subunits that are self-assembled (Step 1) in vivo or on the bench to form the ferritin cage. In the presence of $Fe^{2+}$ (in a typical mammalian cell or in buffer), an iron oxide nanoparticle can be formed within the ferritin core. This magnetic core, formed in Step 2, can be detected using MRI. The conjugation of $NH_2^+$-containing crosslinker (e.g., N,N-dimethyl-1,3-propanediamine (DMPA)), to the outer ferritin surface (Step 3) confers the cationic charge to the apoferritin, which can be measured by zeta potentiometry or isoelectric focusing. Finally, Copper-64 is added to the cationic ferritin by lowering the pH to about 5 to allow adsorption of the Copper-64 to the inner surface (Step 4), forming radioCF. Free Cu-64 is chelated away from the medium and the outer surface of the ferritin, and the ferritin is filtered into a buffer for imaging by either PET or MRI.

150 µL of cationic ferritin (Sigma) underwent buffer exchange from 0.15 M saline to 10 mM sodium acetate buffer at pH 5 through three exchanges using an Amicon-10K (Millipore) centrifugal filter unit with each exchange done at 14000×g for 15 min. Copper-64 (i.e., $^{64}$Cu, Cu-64) in HCL was obtained from the Washington University Cyclotron Facility and diluted with 10 mM sodium acetate buffer, this was then added to the ferritin solution. The reaction was heated to 50° C. for 90 minutes in a Thermomixer. At the end of the reaction, the solution was transferred into a fresh Amicon-10K filter and concentrated at 14000×g for 15 min, the reaction was then rinsed with 150 µL PBS buffer and 150 µL DTPA (diethylenepentaacetic acid) solution. The radioCF was again concentrated at 14000×g for 15 min, then washed again with an additional 300 µL DTPA solution. A third wash using 150 µL PBS and 150 µL DTPA was performed, followed by an additional two washes using 300 µL PBS for each wash. The radioCF was recovered from the Amicon-10K using 150 µL PBS at 1000×g for 2 minutes, then diluted to the final volume with additional PBS. Radiochemical purity was assessed via radioTLC, a 1 µL aliquot was spotted onto a silica gel TLC plate and then developed using 1:1 methanol/10% sodium acetate. Under these conditions radioCF remains at the baseline while unbound Cu-64 travels towards the solvent front, measurement of the radioactivity at the baseline versus other regions provides the radiochemical purity.

To confirm the structure and charge of radioCF after synthesis, dynamic light scattering (DLS) was performed to measure hydrodynamic radius, zeta potentiometry to measure charge, and electron microscopy to confirm that the ferritin structure was not affected by the addition of copper. All characterization was performed using non-radioactive copper (e.g., $^{29}$Cu) for convenience. Average protein size was also characterized using dynamic light scattering (DLS). All samples were prepared to an initial concentration of 1 mg/mL and then directly measured with a Malvern ZEN3600 DLS (Malvern Instruments, Worcestershire, United Kingdom).

Results

RadioCF and radiolabeled native ferritin (radioNF) synthesis was performed by radiolabeling CF or NF under lower pH to incorporate the Cu-64 into the core. The pH was then brought back to neutral and the solution was filtered as described in the Methods. The CF was brown and was readily suspended in PBS. Dynamic light scattering of the radioCF and CF were similar, with an estimated hydrodynamic radius of ~30 nm. The hydrodynamic radius of NF was ~10 nm, suggesting some aggregation in both CF and radioCF. These results were deemed acceptable because of the research group's extensive use of CF to label glomeruli for MRI. The zeta potential of the radioCF was +4 mV, compared to +10 mV for CF and −7 mV for NF, confirming that radioCF was cationic.

Imaging In Vivo Using the radioCF Imaging Agents

Methods

Two studies were performed: Study 1: Healthy male BL6 mice with either CF, native ferritin (NF), or Cu-64; Study 2: male and female Os/+ mice and healthy littermate controls. Os/− mice were obtained from a colony at the University of Virginia. The Os/− mouse is a model of reduced nephron number and glomerular hypertrophy that does not exhibit fibrosis or glomerularlosclerosis. This model has been used in several previous studies using CFE-MRI to measure nephron endowment. The first study was to determine whether radioCF could be used as a targeted contrast agent to label renal glomeruli. The second study was to determine whether dynamic imaging could be used to distinguish mice with reduced nephron mass from healthy controls.

Mice were anesthetized using inhaled anesthetic of 5% isoflurane in an induction chamber and placed on the scanner bed. Anesthesia was maintained during imaging by nose cone. Respiratory rate and basal body temperature were monitored by rectal probe to ensure anesthesia. Mice were and injected with 50-80 µCi of radioCF, radioNF, or Cu-64 by tail vein catheter. Small animal PET imaging was performed on the Siemens Inveon PET/CT 1.5 hr post-injection of radioCF. Images were collected every 5 minutes after injection.

PET images were reconstructed using an ordered subset expectation-maximization (OSEM) algorithm. Static images depicting the biodistribution of radioCF were generated on the Inveon Research Workstation (IRW).

Following PET, the mice were sacrificed. Kidney, liver, lung, heart, brain, pancreas, intestine, and blood were removed and weighed for biodistribution studies.

Biodistribution of each compound was measured in the whole organ with radiophosphorescence imaging using a Typhoon FLA 9500 system. Radioactivity from the Cu-64 was compared to a standard representing the injected dose (ID) to report % ID per g of tissue and % ID per organ. Kidneys were also sectioned at 20 µm thickness and imaged using the same system to localize agent accumulation within the kidney cortex or medulla.

Results

Described here is the synthesis and application of radioCF as an injectable targeted contrast agent to detect renal glomeruli in mice as a first step toward clinical translation. RadioCF and radioNF were injected intravenously into mice and scanned by PET over a 90 minute period. At the final time point, PET images clearly demonstrated selective uptake of radioCF in the renal cortex compared to control, as seen in images of all four mice from each cohort in FIG. 6A-FIG. 6F. RadioNF was also detected by PET in various organs. The primary visually obvious difference between the cohorts outside the kidney was that radioCF was localized the lung, while radioNF and Cu-64 were more detectable in the liver. There was little specific enhancement of the radioNF or free Cu-64 from renal cortex, which was confirmed by examining the time-course of signal changes in each cohort normalized to positron emission from the aorta.

Figures 6A, 6B, 6C, 6D, 6E, 6F, 6G, 6H, 6I:
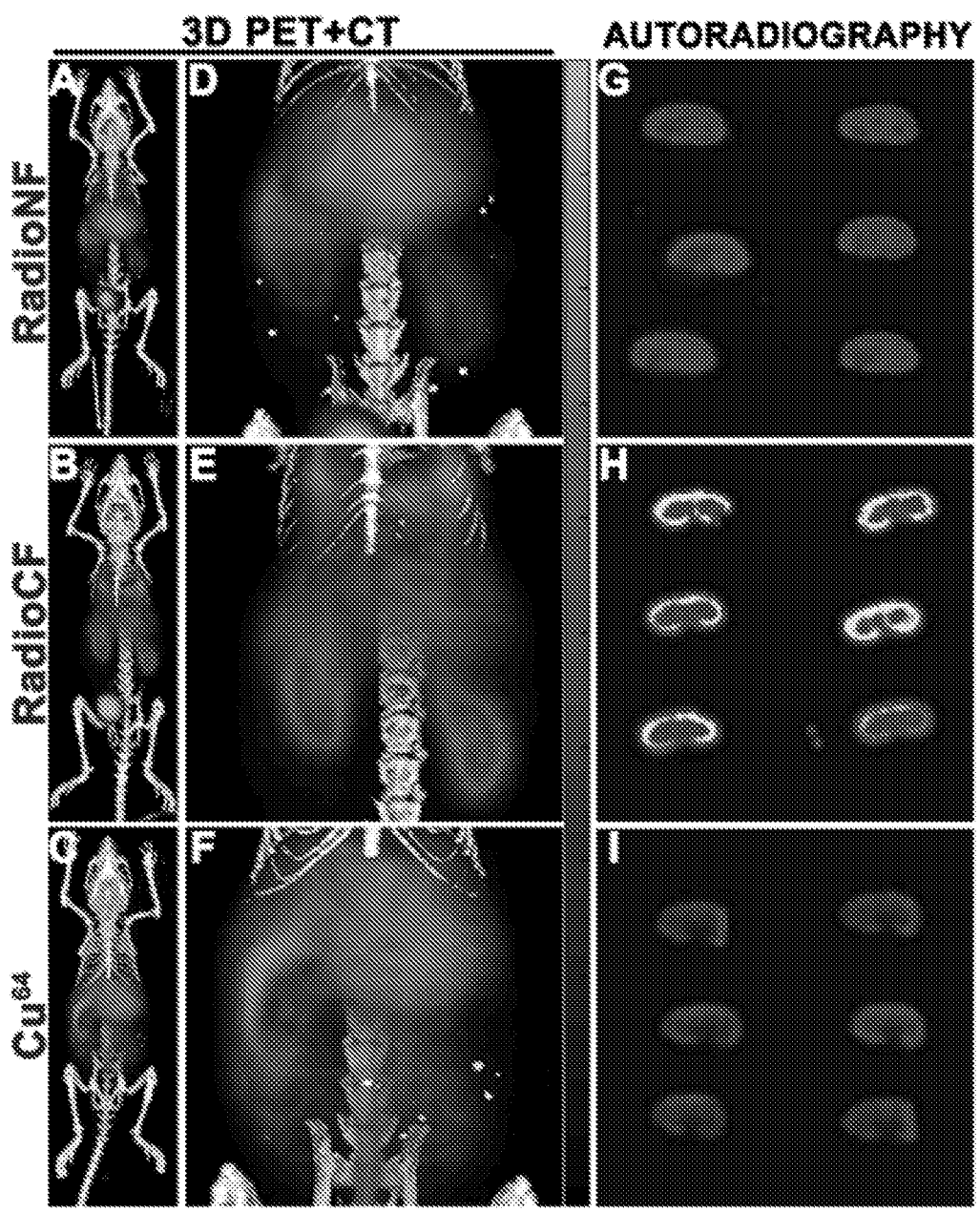
FIG. 6A-FIG. 6I are a series of positron emission tomography (PET) and radiophosphorous imaging after intravenous injection of either RadioNF, RadioCF, or Cu-64 alone. PET images are shown of four mice 90 minutes after injection of RadioNF (A, D), RadioCF (B, E), or Cu-64 (C, F). Arrows in the expanded images of D, E, and F point to the kidney. RadioCF uptake in the kidney was specific to renal cortex, while uptake of RadioNF and Cu-63 was lower and nonspecific. This was confirmed by radiophosporous imaging of 20 μm tissue sections from the same cohorts, shown for a representative animal from each cohort in G-I. Only radioCF was strongly bound to the renal cortex.

Radiophosphorous images of the excised 20 mm sections of the kidneys confirmed the binding of the radioCF, but not NF or Cu-64 alone, to the renal cortex, as seen in FIG. 6G-FIG. 6H. While individual glomeruli were not visible by radiophosphorous, the heterogeneous distribution of radiation in the cortex strongly suggested concentration of the radioCF in the glomeruli.

Figure 7:
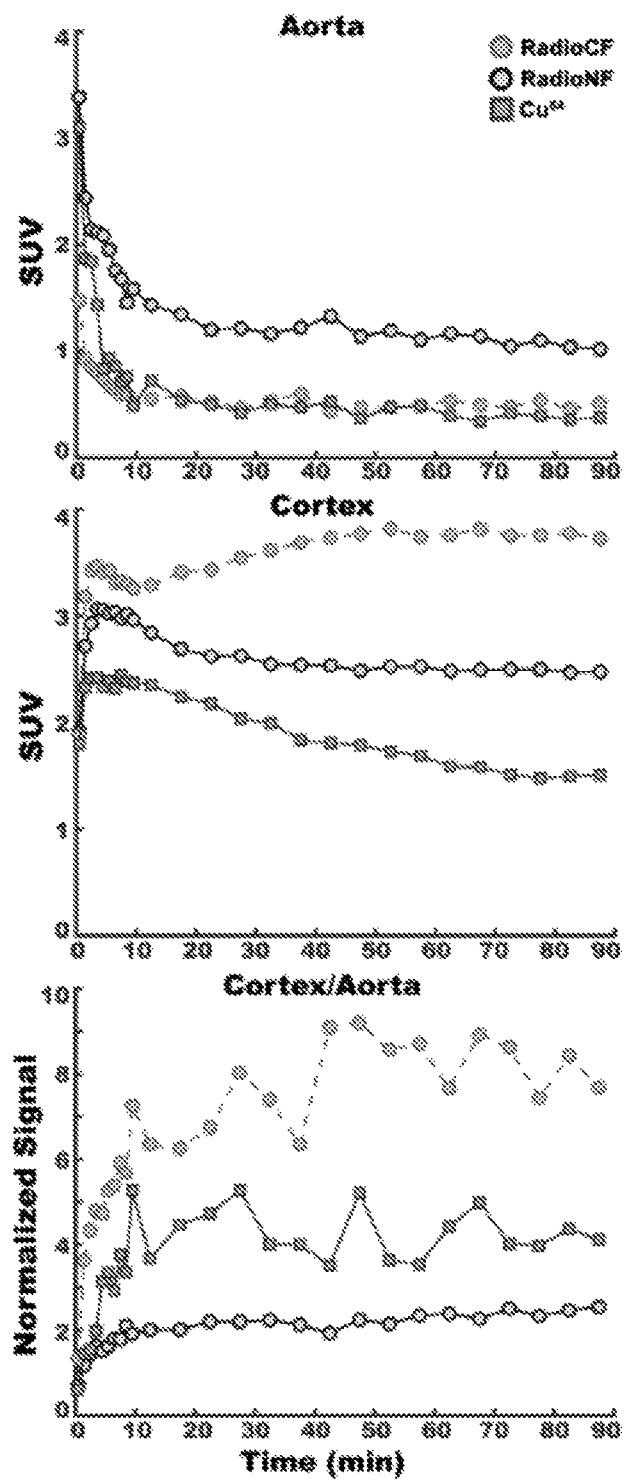
FIG. 7 depicts representative line graphs showing PET signal (AU) over time for the three imaging agents (radioNF, radioCF, and Cu-64 alone).

The time-course of cationic ferritin (CF) uptake was examined using region-of-interest (ROI) analysis in the aorta and in the renal cortex of both kidneys during the PET imaging experiment. Time-courses from each of these ROIs is shown in FIG. 7. The PET signal in the aorta in each cohort was consistent with exponentially decreasing concentration of each of the agents from the blood immediately after injection and a longer circulation of a small fraction of each after the initial decay. In the cortex, the PET signal initially increased in all three cohorts initially after injection, but began to decrease in the radioCF and Cu-64 cohorts after about 15 minutes. However, the signal from cortex in the radioCF cohort continued to increase and remained elevated for the remainder of the study, consistent with retention of the radioCF in the cortex. This specific cortical retention in the radioCF cohort was also clearly observed when cortical signal was normalized to aorta signal.

Figure 8:
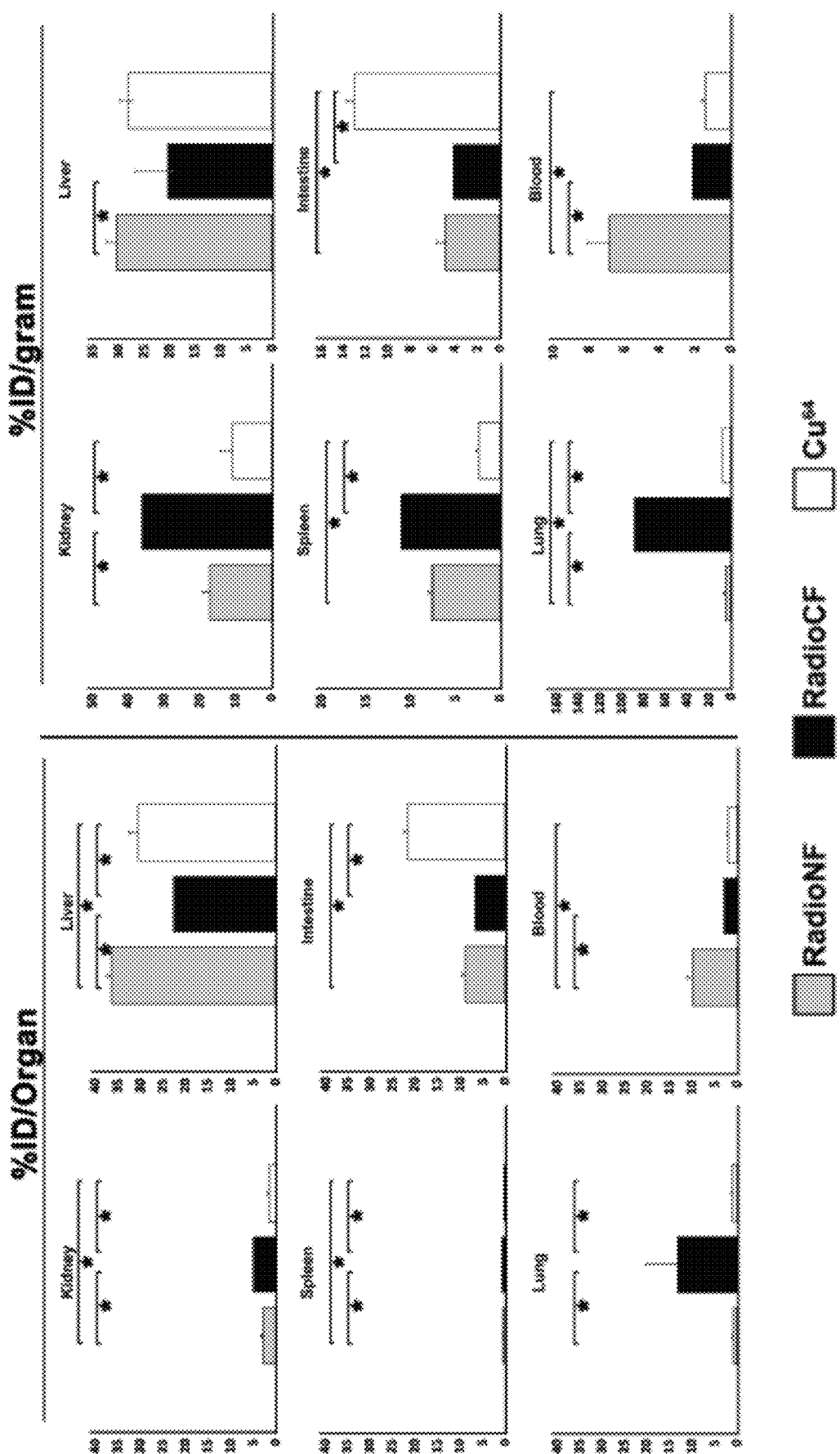
FIG. 8 depicts representative bar graphs showing the percent accumulation obtained by the three imaging agents in vivo in various organ systems, as indicated.

The biodistribution of the radiolabel in each agent was assessed in each intact organ, either as % ID/g of tissue or % ID/organ. These data are shown in FIG. 8 for kidney, liver, spleen, lung, intestine, and blood, with statistically significant ($p<0.05$) and highly statistically significant ($p<0.005$) differences noted for each organ. In the kidney, radioCF was ~100% higher per g and per organ than radioNF. Cu-64 was similar to radioNF. RadioCF was also detected in higher amounts in the lung and spleen, consistent with the PET images. RadioNF was significantly increased in liver and blood. The latter was consistent with the longer blood residence time observed in PET. Cu-64 was significantly elevated in intestine, suggesting rapid liver clearance.

Figures 9A, 9B, 9C, 9D, 9E, 9F, 9G:
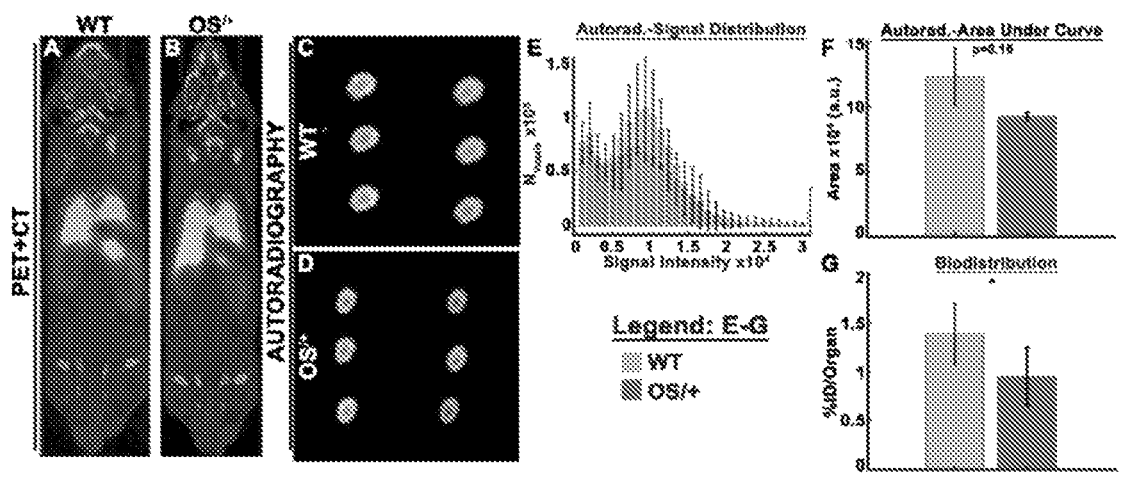
FIG. 9A-FIG. 9G collectively show results for PET imaging of WT or $Os^{/+}$ mice treated with radio-CF.
Figure 9H:
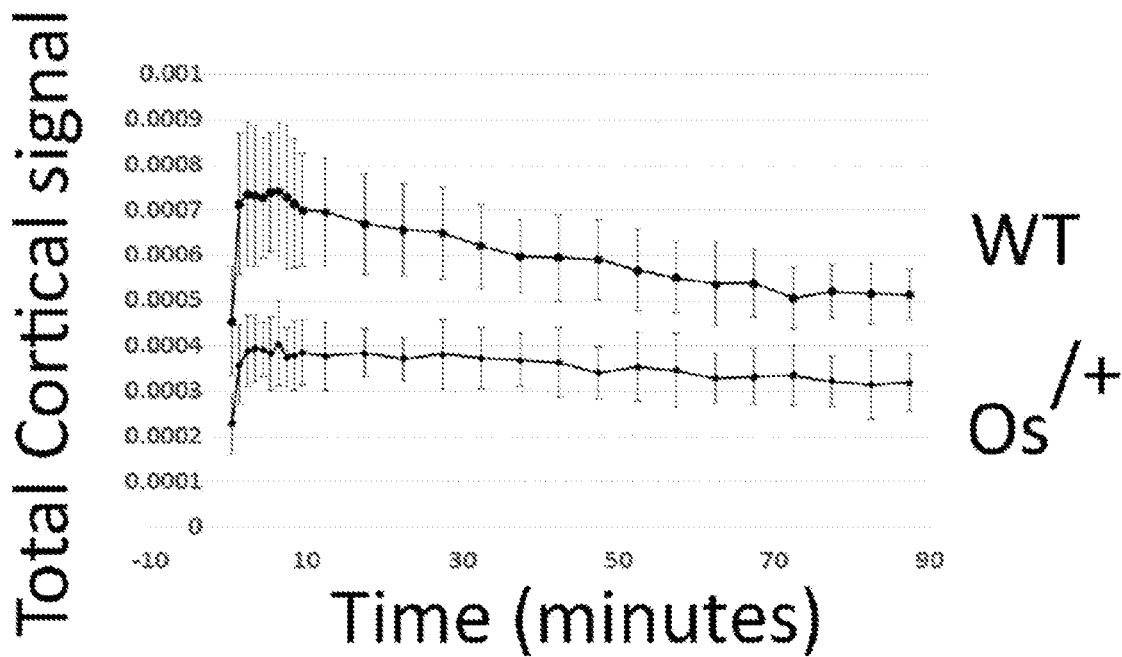
FIG. 9H-FIG. 9I show line graphs depicting total cortical signal over time (H), or PET signal over time (I) in each population.
Figure 9I:
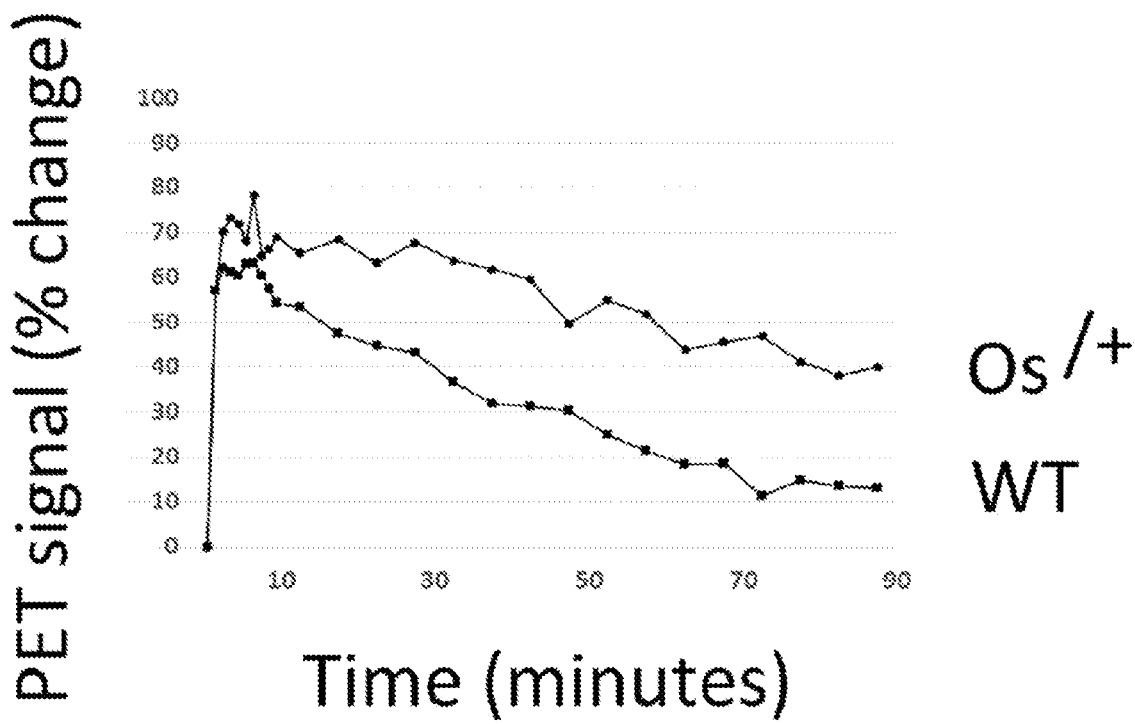

The use of radioCF to measure differences between healthy and OS/−mice with nephron reduction was examined. Here, total renal cortical uptake of CF was examined, taking into account the difference in kidney size between the WT and OS/+ mice. Similar to what was observed in the experiments comparing radioCF, radioNF and Cu-64, radioCF accumulated in the renal cortex and was visible by PET by 90 minutes in both WT and Os/+ mice, as seen in FIG. 9A-FIG. 9B. The difference in kidney sizes were apparent in radiophosporous imaging of tissue sections, shown in FIG. 9C-FIG. 9D. The primary difference between the cohorts was the total accumulation of radioCF in the kidney cortex, shown in the time-courses of FIG. 9H-FIG. 9I. Total signal in the cortex was consistently higher in the WT mice over the duration of the experiment, consistent with the larger number of glomeruli in the WT mice compared to OS/−. However by 90 minutes after the first injection, radioCF accumulation in the OS/+ mouse kidney was approximately 60% over that of the first time point at 5 minute. RadioCF signal in the WT mice was retained at approximately 10% of the first time point. Importantly there were no significant differences per-voxel in radioCF accumulation by 90 minutes.

Figures 11A, 11B, 11C, 11D, 11E, 11F:
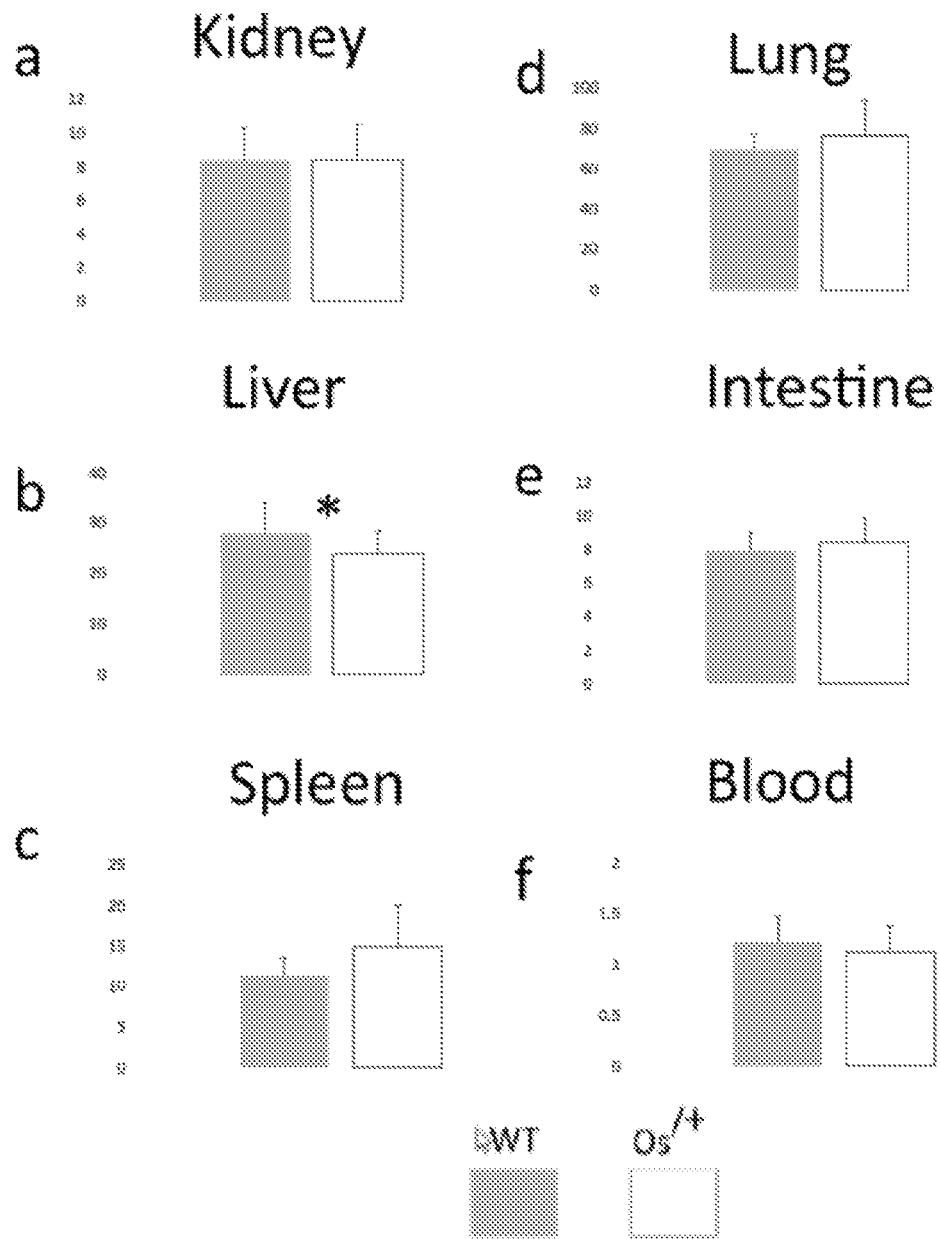

The biodistribution of radioCF after imaging was consistent with the observations by PET. % ID/g was not significantly different in WT and OS/+ mice in kidney, and only slightly lower in liver in the OS/+ mice (see e.g., FIG. 11B). % ID/organ was significantly lower by about 50% in OS/+ kidney (see e.g., FIG. 11G). There were no other statistically significant differences in biodistribution between the two cohorts.

DISCUSSION

This example describes the formation of a glomerulus-targeted contrast agent for PET, radioCF, based on the use of cationic ferritin radiolabeled with Cu-64, stably incorporated into its core. RadioCF was intravenously injected into healthy B6 mice and demonstrated selective accumulation in the renal cortex compared to radioNF and Cu-64-injected controls. In a separate study, radioCF accumulation in the renal cortex of OS/+, a mouse model of reduced nephron mass without proteinuria or glomerulosclerosis, was reduced compared to littermate controls. Total radioCF accumulation in the Os/− mouse kidney was reduced, but CF was retained for longer than in WT, suggesting a possible compensatory mechanism to maintain total renal filtration over time despite reduced nephron mass. Overall, this work provides evidence that radioCF may be applied to monitor nephron mass or renal mechanisms of filtration associated with compensation for nephron loss.

This describes the development of radioCF and CF as a diagnostic tool for use in humans. The advantage of PET over MRI is its exquisite sensitivity, allowing detection in sub-pM concentrations. RadioCF was detected in doses comparable to microdoses (<100 μM) typically applied for an exploratory new drug.

Detecting the accumulation of CF and the timecourse of its accumulation and traversal of the glomerular basement membrane is thought to provide a new view of several processes in vivo: 1) The relationship between bulk glomerular filtration and renal microstructure in health and disease, 2) The relationship between macromolecular and glomerular filtration, and 3) The structure of the glomerular basement membrane in pathology. The ability to monitor these processes can be important for diagnosis and monitoring of acute or chronic kidney disease, identifying patients at risk for chronic kidney or cardiovascular disease, and improving transplant matching by systematic and more accurate analysis of allograft tissue.

RadioCF is a radiolabeled form of CF, which has been developed as a targeted natural nanoparticle contrast agent to measure nephron number and glomerular volume in the intact kidney with MRI. The ferritin molecule has several advantages: it is a natural contrast agent that can be expressed recombinantly, it is also water soluble, readily functionalized, and contains a modifiable ~8 nm core that allows for deposition of metals and other compounds. The size of ferritin allows it to traverse the glomerular endothelial fenestrae and bind transiently to various components of the GBM. The dynamics of CF accumulation and turnover in the GBM may reveal mechanisms of extracellular matrix dynamics or remodeling during pathology or therapy.

One potential use of radioCF is to estimate nephron mass and to detect its heterogeneity in tissue. In humans, this is an important step toward nondestructive imaging as a means to avoid the tissue damage and sample error characteristic of traditional biopsy. RadioCF-PET may also expand the patient population that can be evaluated. Imaging may be useful in patients that are potentially at risk for kidney disease but who do not yet exhibit either gross proteinuria or changes in glomerular filtration rate (GFR) that would recommend a biopsy.

While the goal of this work was to develop radioCF for PET, the iron oxide nanocrystal in the core of radioCF allows it to serve as a combined PET/MRI agent. This can be useful for validating estimates of nephron mass and changes in contrast agent distribution detected by PET using the higher-resolution MRI. This validation is critical for biomarker development. It is presently believed that CF, not radiolabeled, can be mixed with the initial dose of radioCF and then imaged with PET and MRI simultaneously. Alternatively, the higher dose of CF may be given after radioCF-PET.

It is imperative to evaluate the toxicity of any candidate agent, in preclinical or clinical applications. Here is reported several investigations of CF toxicity in rodents, including rats, mice, and kidneys, in relatively high MRI detectable doses of 5.75 mg/100 g. The results have generally demonstrated minimal toxicity using horse spleen derived CF in rabbits that is abrogated by steroids, suggesting that the foreign nature of the CF had caused the reaction.

Example 4: Cu-64-Labeled Cationic Ferritin (Radiocf) as a Targeted Contrast or Imaging Agent This example describes the development of a radiolabeled cationic ferritin and the use of positron emission tomography (PET) to detect the radiolabeled cationic ferritin. Here, it was shown that the imaging or contrast agent can be used to detect kidney glomeruli with PET.

INTRODUCTION

Nephrons are the functional units of the kidney responsible for maintaining blood electrolyte homeostasis and osmolarity. At full-term, humans are born with a full complement of nephrons, but nephron endowment ranges from ~200,000 to over 2,000,000 between individuals. This range may in part explain variability in susceptibility to chronic kidney and cardiovascular disease throughout life. Nephron loss can occur with aging or due to injury. Premature infants, for example, are susceptible to renal damage and nephron loss due to common nephrotoxic medications. Loss of nephrons can lead to short-term compensation of other nephrons, through hyperfiltration, to maintain glomerular filtration rate. This compensatory hyperfiltration is thought to result in further nephron loss due to damage to the remaining renal glomeruli and tubules, leading eventually to kidney disease and end stage renal disease requiring dialysis or transplant.

Much of the understanding of the role of nephron number in human health has been achieved through postmortem analysis using stereological techniques. While these are crucially important, they are destructive and cannot generally be applied in vivo. Because of the impact of chronic kidney disease (CKD), which afflicts approximately 15% of the world population, it is critical to establish new diagnostic tools to understand and monitor nephron number in patients at risk for CKD or in transplant recipients.

Several radiological imaging approaches have been used to estimate nephron number based on surrogates like cortical or kidney volume, or through a combination of biopsy and x-ray computed tomography. Recently nephron number has been directly measured in vivo using magnetic resonance imaging (MRI) with intravenously injected cationic ferritin (CF). Ferritin is an iron storage protein that occurs naturally in all mammals, including humans. Intravenously injected CF binds to the glomerular basement membrane and temporarily provides image contrast between the glomeruli and the surrounding tissue in 3D gradient-recalled echo MRI. Individual glomeruli are then identified from the images using software, and individual glomerular volumes can be measured and spatially mapped. Importantly, cationicferritin enhanced MRI (CFE-MRI), can be combined with other MRI pulse sequences to provide an integrated view of vascular, glomerular, and possibly tubulointerstitial microstructure. This combined approach has the potential to inform a new class of studies in the kidney that explore spatiotemporal changes in tissue structure and physiology during development of disease and in response to therapy. Further, CFE-MRI opens the possibility of measurement of nephron number as a clinical marker of renal health in patients at risk for CKD, and in transplant recipients.

One of the potential difficulties of CFE-MRI in clinical translation is the relatively high dose of the current formulation of CF required to overcome detection limits of MRI. Most studies have used the contrast agent in doses of ~5 mg/100 g body weight in rodents and in donor human organs or about 30 mg/100 g in humans. There are several techniques that allow for detection in ~10-100 fold lower doses, but these techniques so far report low yields during synthesis. The driving factor for the reducing the amount of CF needed for glomerular contrast with MRI is the relaxivity of the agent, improved sensitivity could be obtained by increasing iron deposition in the core or by modifying the chemical makeup of the particles. Custom hardware and software may need to be integrated with clinical imaging systems. Given the current detectable doses of CFE-MRI, the roadmap toward translation to clinical use is challenging.

As described herein, an alternative to improving CF relaxivity, is the incorporation of nuclear imaging. Described herein is a novel synthesis of CF labeled with Cu-64, a positron-emitting isotope commonly utilized in positron emission tomography (PET). This new agent, RadioCF, can also be used as a combined PET-MRI agent, and thus can inform early biodistribution and toxicity studies for CFE-MRI. While PET does not offer the spatial resolution and adjustable tissue contrast of MRI, it has the advantage of allowing detection of agents in doses below those considered trace quantities in the US FDA requirements for an exploratory investigational new drug. RadioCF-PET may thus be rapidly translated to early clinical use, and may provide a useful marker for nephron number in humans. Here it was demonstrated that the synthesis and application of RadioCF as an injectable targeted contrast agent can detect renal glomeruli in mice, which can be potentially used in direct measurement of nephron number, in vivo, in humans.

Methods

RadioCF Synthesis

FIG. 1 illustrates the concept of RadioCF synthesis. Apoferritin subunits that are self-assembled (Step 1) in vivo or on the bench to form the ferritin cage. In the presence of $Fe^{2+}$ (in a typical mammalian cell or in buffer), an iron oxide nanoparticle is formed within the ferritin core. This magnetic core, formed in Step 2, can be detected using MRI. The conjugation of $NH^{2+}$-containing crosslinker to the outer ferritin surface (Step 3) confers the cationic charge to the apoferritin, which can be measured by zeta potentiometry or isoelectric focusing. Finally, Cu-64 is incorporated within the cationic ferritin by lowering the pH swelling the proteinaceous subunits and allowing adsorption of the Cu-64 (Step 4), forming radioCF. Unincorporated, "free" Cu-64 is complexed by the addition of an added chelating ligand and separated from the radioCF via size exclusion chromatography. Fractions containing pure radioCF are combined, concentrated and diluted with appropriate buffer for imaging by either PET or MRI.

150 μL of cationic ferritin was exchanged (CF; Sigma) from 0.15 M saline into 10 mM sodium acetate buffer at pH 5 using an Amicon-10K (Millipore) centrifugal filter, and centrifuged at 14000×g for 5 min. The exchange process was repeated three times, at the end of the exchange process the CF was rinsed from the filter and the volume adjusted to 400 μl with additional 10 mM sodium acetate buffer at pH 5. The CF solution is allowed to sit overnight at pH 5, allowing for the subsequent labeling with Cu-64. Cu-64 in 0.1 M HCl was obtained from the Washington University Cyclotron Facility, diluted with 100 μl 10 mM sodium acetate buffer pH 5, then added to the ferritin solution. The solution was heated to 50° C. for 90 minutes in an Eppendorf Thermomixer C. The reaction was then cooled to 25° C., the pH raised with the addition of 6 μL 1 N NaOH and 15 μL 10 mM DTPA (diethylenepentaacetic acid). The reaction was then mixed for an additional 15 minutes. The radioCF was then purified on a disposable BioRad column packed with 2 g of Sephadex G-25 superfine resin preswollen overnight with MilliQ water. The reaction was applied to the column bed and then gravity eluted with 1 mL fractions of MilliQ water. RadioCF is typically eluted in fractions 10-12, these fractions are combined and the radioCF concentrated using an Amicon Ultra-15 filter centrifuged at 5000×g for 8 min.

Radiochemical purity was assessed via radio thin layer chromatography. A 1 μL aliquot was spotted onto a silica gel TLC plate and developed using 1:1 methanol/10% sodium acetate. Under these conditions radioCF remained at the baseline while DTPA complexed Cu-64 traveled towards the solvent front. Measurement of the radioactivity at the baseline versus other regions provided radiochemical purity.

RadioNF Synthesis

RadioNF, radiolabeled native ferritin, was prepared in the identical process described for radioCF. Native ferritin (nF; Sigma) underwent buffer exchange to 10 mM sodium acetate buffer at pH 5 followed by radiolabeling using Cu-64.

Characterization of RadioCF

All characterization was performed using non-radioactive copper, $CuCl_2$ dissolved in 0.5 M HCl. The [Cu] was adjusted to result in a total of 0.4 μg, the radiolabeling procedure was then followed using a cold Cu stock solution. The purified cold radioCF was then subjected to dynamic light scattering (DLS) to measure hydrodynamic radius, zeta potentiometry to measure charge, and transmission electron microscopy (TEM) to confirm ferritin structure had not been altered during incorporation of copper. DLS and zeta potentiometry were performed on 1 mg/mL samples in a plastic zeta cell using a Malvern ZEN3600 DLS (Malvern Instruments, Worcestershire, United Kingdom). TEM was performed with a JEOL JEM-1400 120 kV TEM (JEOL, Ltd.; Tokyo, Japan).

Magnetic resonance imaging (MRI) was performed on a radioCF-labeled mouse kidney to confirm the specific binding of radioCF to glomeruli and to confirm radioCF could still also be used as a MRI contrast agent. The mouse received a dose of 0.05 mg of radioCF intravenously and was perfused with saline followed by formalin. Kidneys were resected and imaged on an Agilent 11.74 T DirectDrive MRI (Palo Alto, CA) using a 3D gradient recalled echo pulse sequence.

PET Imaging

Two separate studies were performed: Study 1: Healthy male C57/BL6 mice with either radioCF, radio native ferritin (radioNF), or free Cu-64; Study 2: male and female Os/+ mice and healthy littermate controls. Os/+ mice were obtained from a colony at the University of Virginia and mutation was confirmed by the syndactylism of their toes. The Os/+ mouse is a model of reduced nephron number and glomerular hypertrophy that does not exhibit fibrosis or glomerulosclerosis. Study 1 was to determine whether radioCF could be used as a targeted contrast agent to label renal glomeruli. Study 2 was to determine whether dynamic imaging could be used to distinguish mice with reduced nephron mass from healthy controls.

Mice were anesthetized using inhaled anesthetic of 1-2% isoflurane in an induction chamber and placed on the scanner bed. Anesthesia was maintained during imaging by nose cone. Respiratory rate and basal body temperature were controlled and monitored to ensure anesthesia. Mice were and injected with 50-80 µCi of radioCF, radioNF, or Cu-64 by tail vein catheter, Small animal PET imaging was performed on the Siemens Inveon PET/CT for 1.5 hr post-injection of radioCF. After injection, images were collected every five minutes and then every ten minutes for the remaining time until 1.5 hr post injection. PET images were reconstructed using an ordered subset expectation-maximization algorithm. Static images depicting the biodistribution of radioCF were generated on the Inveon Research Workstation (Siemens).

Following PET, the mice were sacrificed by cervical dislocation under isoflurane anesthesia. Kidney, liver, lung, heart, brain, pancreas, intestine, and blood were removed and weighed for biodistribution studies. Radioactive biodistribution of radioCF in each whole organ was measured/counted on a Beckman 8000 gamma counter. Radioactivity from the Cu-64 was compared to a standard representing the injected dose (ID) to report % ID per g of tissue and % ID per organ. Kidneys were cut in half and one half frozen and sectioned at 20 µm thickness on a Leica CM 1860 cryostat. Kidney sections were then imaged with radio-phosphorescence imaging using a Typhoon FLA 9500 system to localize agent accumulation within the kidney cortex or medulla.

Glomerular Filtration Rate

Glomerular filtration rate (GFR) was measured in a separate cohort of WT and OS/+ mice. GFR was measured from elimination kinetic curves acquired using a transdermal device (MediBeacon, Mannheim, Germany) detecting fluorescent isothiocyanate (FITC)-labeled sinistrin (Fresenius-Kabi; Austria, Linz) in the blood. Briefly, a region of fur on the animal was removed. The monitor was attached with an adhesive patch from MediBeacon. The animal received FITC-labeled sinistrin (7.5 mg/100 g body weight) by tail vein. Fluorescence intensity was measured for 75-90 minutes. Kinetic curves were analyzed using the MPD Studio software (Mannheim Pharma and Diagnostics, Amtsgericht Mannheim, Germany). The formula to determine GFR was derived from the half life as follows, $$GFR = 14616.8/(t_{1/2,FITC}). \tag{1}$$

Here, GFR is in units of (µl*min*100 gBW), the constant 14616.8 has units of mcl/100 g BW, and $t_{1/2\text{-}FITC}$, the half-life of FITC-sinistrin, has units of minutes.

Post Processing

Data were normalized to standardized uptake values (SUV) for each animal data set using the animal's weight and dose received. In study 1, 3D regions of interest (ROIs) were drawn on the renal cortex and the descending aorta using Inveon Research Workplace software (Siemens). In study 2, renal cortex was segmented and each voxel time course in the kidney cortex from PET imaging experiments were fitted with a bi-exponential model, $$f(x) = C1 \cdot (e^{-C3(t-C2)} - e^{-C4(t-C2)}) + C5. \tag{2}$$

Here, C1 is a scaling constant, C3 is the decay rate of signal after peak, C4 is the rise rate to peak, C5 is an additive constant and C2 is a time shifting constant. Fitted parameters were plotted as histograms for each cohort (WT vs. Os/+). A paired two tail student's t-test was used to compare the overlapping bins in the histograms for each fitted parameter between cohorts.

Results

RadioCF and radioNF synthesis were performed by radio-labeling CF or NF to incorporate the Cu-64 into the core. The radioCF solution was brown, consistent with commercial solutions, and was readily suspended in sterile saline Dynamic light scattering of the radioCF and CF were similar, with an estimated hydrodynamic radius of ~30 nm. The hydrodynamic radius of NF was ~10 nm, suggesting some aggregation in both CF and radioCF (see e.g., FIG. 5). RadioCF samples also contained a second population with a hydrodynamic radius of ~500 nm, suggesting some increased flocculation in solution compared to commercial CF. The zeta potential of the radioCF was +6.3 mV, compared to +33.3 mV for CF and −15 mV for NF, confirming that radioCF was cationic (see e.g., FIG. 5). TEM confirmed similar spherical molecular structure of the ferritin and a core diameter of ~7 nm in both NF and radioCF (see e.g., FIG. 5).

Figure 5:
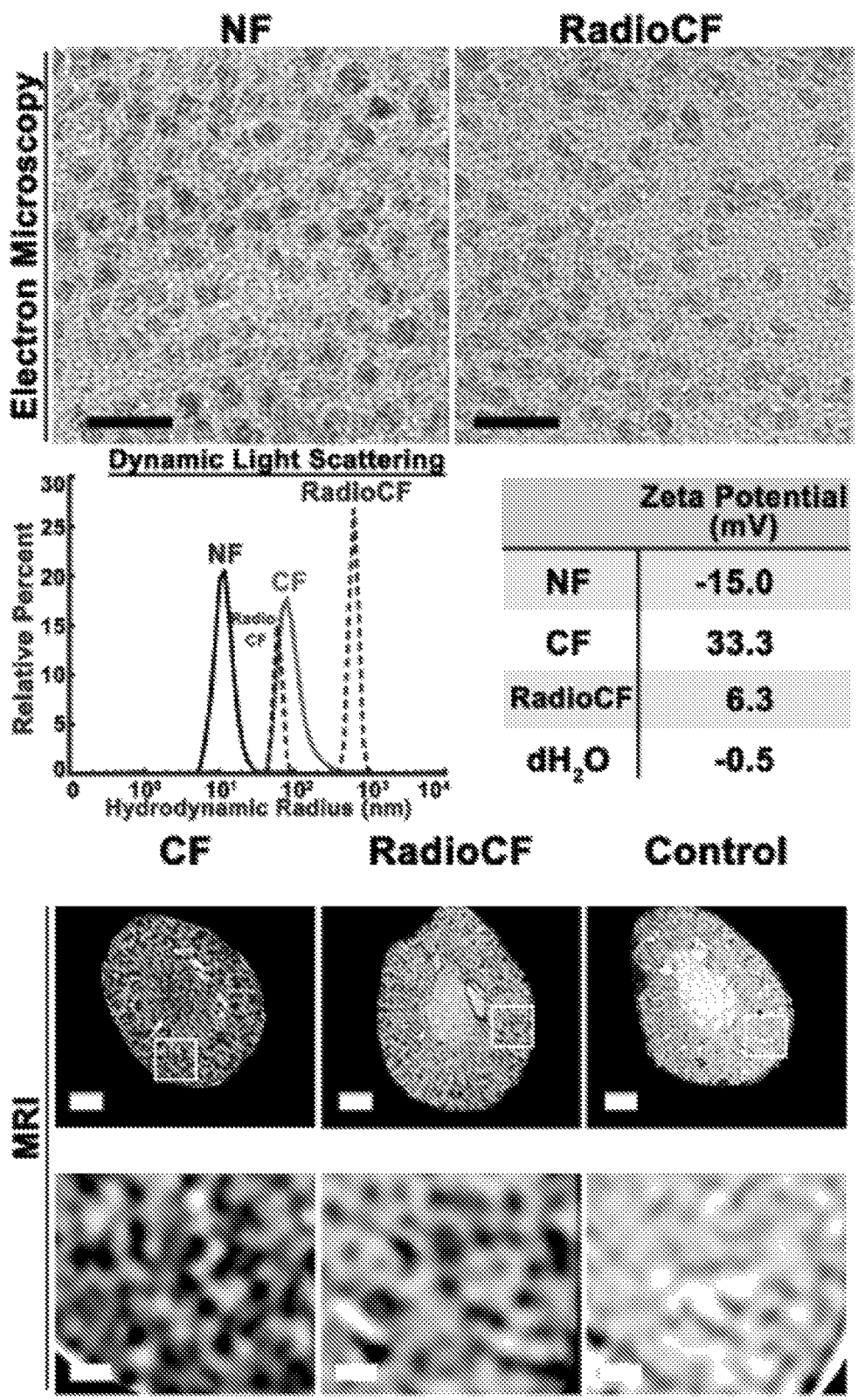
FIG. 5 is a series of electron microscopy images, a graph of zeta potential measurements, and MRI images.

MRI of a mouse kidney that received a large dose of RadioCF exhibited dark punctate labeling of glomeruli throughout the kidney cortex (see e.g., FIG. 5). This is consistent with the labeling seen in mice kidneys that receive normal CF. Such labeling was not seen in the control.

Study 1

RadioCF, radioNF, and free Cu-64 were injected intravenously into mice and scanned by PET over a 90 minute period. At the final time point, PET images clearly demonstrated selective uptake of radioCF in the renal cortex compared to radioNF- or Cu-64-injected controls, as seen in images of all four mice from each cohort in FIG. 6A-FIG. 6F. The primary visible difference between the cohorts outside the kidney was that radioCF was also localized in the lung, while radioNF and Cu-64 were localized to the liver. There was little specific enhancement of the RadioNF or free Cu-64 from renal cortex, confirming that only radioCF labeled the cortex.

Radiophosphorous images of excised 20 µm sections of the kidneys confirmed the binding of the radioCF alone and not NF or Cu-64 to the renal cortex, as seen in FIG. 6G-FIG. 6I. Individual glomeruli were not visible in radiophosphorous images, but the distribution of radiation in the cortex strongly suggested concentration of the radioCF in the glomeruli.

The time course of radioCF uptake was examined using region-of-interest (ROI) analysis in segmented regions for the aorta (blood pool) and in the renal cortex of both kidneys during PET. Mean of all time courses from each of these ROIs is shown in FIG. 7. The PET signal in the aorta in each cohort and for each agent was consistent with exponentially decreasing concentration after injection plus a longer circulation of a small fraction of agent after the initial decay. In the cortex, the PET signal increases immediately after injection of either radioCF or Cu-64 in all three cohorts. However, the signal in the cortex in the radioCF cohort continued to increase and remained elevated for the remainder of the study, consistent with retention of the radioCF in the cortex. Signal in the cortex in the Cu-64 cohort decreased for the remainder of the study, and eventually returning to baseline signal (signal at t=0 min). The specific cortical retention in the radioCF cohort was also clearly observed in autoradiography (see e.g., FIG. 9C, FIG. 9D).

The biodistribution of radioCF, radioNF, and Cu-64 were assessed in each intact organ as percent-injected dose per gram (% ID/g) of tissue or percent-injected dose per organ (% ID/organ). These data are shown in FIG. 8 for kidney, liver, spleen, lung, intestine, and blood, with statistically significant ($p<0.05$) and highly statistically significant ($p<0.005$) differences noted for each organ. In the kidney, radioCF was ~ 100% higher per gram and per organ than radioNF. In the kidney, Cu-64 was similar to radioNF. RadioCF was also detected in higher amounts in the lung and spleen compared to both RadioNF and Cu-64, consistent with the PET images. RadioNF was significantly increased in liver and blood compared to radioCF. The latter was consistent with the longer blood residence time observed in the mean time-course taken from the aorta in PET images (see e.g., FIG. 7). Cu-64 was significantly elevated in intestine, suggesting rapid liver clearance.

Study 2

It was examined whether radioCF-PET could distinguish healthy WT mice and OS/+ mice with reduced nephron number. Here total renal cortical uptake of CF was examined, taking into account the % difference in kidney size between the WT and OS/+ mice. Similar to what was observed in the experiments comparing radioCF, radioNF and Cu-64, radioCF accumulated in the renal cortex and was visible by PET by 90 minutes in both WT and Os/+ mice, as seen in FIG. 9A-FIG. 9B. The differences in kidney size were apparent in radiophosporous imaging of tissue sections, shown in FIG. 9C-FIG. 9D. The primary difference between the cohorts was the total accumulation of radioCF in the kidney cortex, shown in the time courses of FIG. 9E-FIG. 9F. Total signal in the cortex was consistently higher in the WT mice throughout the experiment, consistent with a larger number of glomeruli per voxel in the WT mice compared to OS/+. However by 90 minutes after the first injection, radioCF accumulation in the OS/+ mouse kidney was approximately 60% over baseline signal at 5 minutes. RadioCF signal in the WT mice was retained at approximately 10% of the first time point. Importantly there were no significant differences per-voxel in radioCF accumulation by 90 minutes. Mean GFR in separate WT and OS/+ cohorts were 237.7 and 173.4 µL*min$^{-1}$, respectively.

The biodistribution of radioCF after imaging was consistent with observations by PET. Total signal in autoradiography images confirmed WT mouse kidneys having increased total retention of radioCF compared to OS/+ mouse kidneys (see e.g., FIG. 9C-FIG. 9D). Biodistribution measured by % ID/g was not significantly different in WT and OS/+ mice in kidney, and was only slightly lower in the liver in OS/+ mice. % ID/organ was significantly lower by about 50% in OS/+ kidney (see e.g., FIG. 8). Sections from WT kidneys, on average, had a larger area under the curve of signal intensity compared to similar sections obtained from OS/+ kidneys (see e.g., FIG. 9F). There were no other statistically significant differences in biodistribution between the two cohorts.

Figure 10:
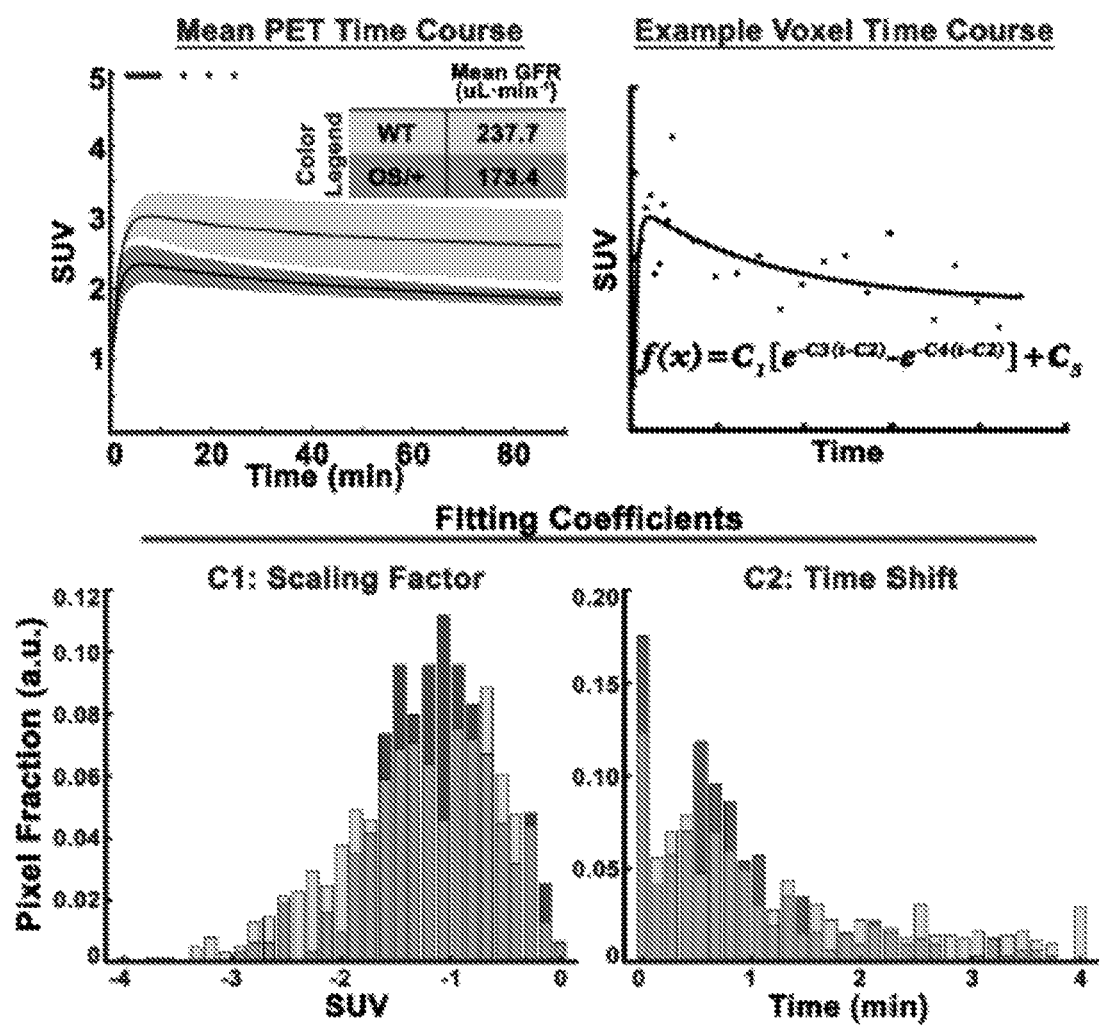
FIG. 10 is a series of graphs showing a bi-exponential model fitted to time courses from normalized dynamic PET imaging data in WT and OS/+ mice that received radioCF and distributions of fitted model parameters.

A bi-exponential model was fitted to time courses from normalized dynamic PET imaging data in WT and OS/+ mice that received radioCF (FIG. 10). Distributions of fitted model parameters are plotted in FIG. 10. From the coefficients calculated from fitting, differences were observed in the absolute mean of the scaling constant C1 and the delay time constant C2 between WT and OS/+ mice. The absolute mean value for the distribution of the constant C1, the magnitude of the normalized PET signal, increased for the WT cohort compared to the OS/+ cohort. The mean value of C2, the delay time in the dynamic curve, was also higher in WT compared to the Os/+ mice.

DISCUSSION

This work describes the creation of a glomerulus-targeted contrast agent for PET, radioCF, based on the use of cationic ferritin with Cu-64 stably incorporated into its core. RadioCF was intravenously injected into healthy C57/BL6 mice and demonstrated selective accumulation in the renal cortex compared to radioNF and Cu-64-injected controls. In a separate study, radioCF accumulation in the renal cortex of OS/+ mice, a mouse model of reduced nephron mass, was lower compared to controls. PET signal was observed to be ~25% lower in OS/+ mice while mean GFR was measured to decrease by almost 40% in OS/+ mice compared to WT, suggesting a possible compensatory mechanism to maintain total renal filtration over time despite reduced nephron mass. The difference in the delay times between WT and OS/+ mice, it is believed, also points the difference in total nephron number. A reduced nephron number would take less time for the injected agent to reach peak for the loading of the agent onto all glomeruli. This work demonstrates that radioCF may be used to monitor nephron mass or detect altered renal filtration in compensation for nephron loss.

This work describes the development of radioCF and CF as a diagnostic tool that can be translated to humans. The advantage of PET over MRI is its sensitivity, allowing detection in sub-pM concentrations. Here radioCF was detected in doses comparable to microdoses (<100 µM) typically applied for an exploratory new drug application with the U.S. Food and Drug Administration. Detecting the accumulation of CF and the time course of its accumulation and traversing the glomerular basement membrane is thought to provide a new view of several processes in vivo: 1) The relationship between bulk glomerular filtration and renal microstructure in health and disease, 2) The relationship between macromolecular and glomerular filtration, and 3) The structure of the glomerular basement membrane in pathology. The ability to monitor these processes may be important for diagnosis and monitoring of acute or chronic kidney disease, identifying patients at risk for chronic kidney or cardiovascular disease, and improving transplant matching by systematic and quantitative assessment of allografts.

RadioCF is a radiolabeled form of CF, which has been developed as a targeted natural nanoparticle contrast agent in the intact kidney with MRI. The ferritin molecule has several advantages that may suggest its use in humans: it is a natural contrast agent that can be expressed recombinantly and it is also water soluble, readily functionalized, and contains a ~8 nm hallow core that allows for deposition of metals and other compounds of various amounts. The size of ferritin allows it to traverse the glomerular endothelial fenestrae and the cationic modification of the surface enables it to bind transiently to various components of the GBM. The dynamics of CF accumulation and turnover in the GBM may reveal mechanisms of extracellular matrix dynamics or remodeling during pathology or therapy. An example of one use of radioCF can be to estimate nephron mass and to detect its heterogeneity throughout the kidney. In humans, this is an important step toward using nondestructive imaging as a means to avoid the tissue damage and sample error characteristic of traditional biopsy. RadioCF-PET may also expand the patient population that can be evaluated, imaging may be useful in patients that are potentially at risk for kidney disease but who do not yet exhibit either gross proteinuria or changes in GFR that would recommend a biopsy. This method could provide for a way to increase the number of potential kidney donors that might be considered marginal from other currently practiced methods.

The iron oxide nanocrystal retained in the core of radioCF allows it to serve as a combined PET/MRI agent. This can be useful for validating estimates of nephron mass and changes in contrast agent distribution detected by PET using the higher-resolution MRI. This validation is critical for biomarker development. It is envisioned that normal CF, not radiolabeled, can be mixed with the initial dose of radioCF and then imaged with PET and MRI simultaneously. Alternatively, the higher dose of CF may be given after radioCF-PET. Investigations of the use of radioCF may guide future studies in non-radioactive CF that can guide its clinical translation.

It is imperative to evaluate the toxicity of any candidate agent, in preclinical or clinical applications. The methods described herein can provide a method for detection with a reduced radiation dose due to the targeted nature of the imaging agent. The inventors have reported several investigations of CF toxicity in rodents, including rats, mice, and kidneys, in relatively high MRI detectable doses of 5.75 mg/100 g. The results have generally demonstrated minimal toxicity using horse spleen derived CF in rabbits that is abrogated by steroids, suggesting that the foreign nature of the CF had caused the reaction. In principle this should be minimized if CF or radioCF is formed recombinantly to match the species. For radioCF, detection of trace doses using PET should minimize potential for toxicity at the early stages of translation.

In conclusion, radioCF is a targeted contrast agent for imaging to detect nephron mass by PET or by PET/MRI. The high sensitivity of radioCF-PET may make it ideal for future work aimed at development of nephron mass as a marker of kidney health and viability in humans.

Example 5: Radiolabeled Recombinant Ferritin

The following example describes the synthesis and detection of recombinant ferritin with an iron oxide nanoparticle core comprising Cu-64.

It was discovered that the recombinant ferritin cage had to be opened up by a reduced pH in order to incorporate the radiolabel into the recombinant ferritin and absorbed onto the surface of the iron core.

Because the heavy chain (HC)-light chain-(LC) ferritin fusion protein had never been expressed in *E. coli*, it was unclear if it would self-assemble in the bacteria to form a natural 24mer human recombinant molecule. However, recombinant human ferritin was readily expressed and purified from *E. coli*. First, recombinant human fusion protein was attempted to be formed by expressing apoferritin in *E. coli* under low iron conditions. This would allow us to load the core with an iron oxide and the radiolabel at a later time. However, it was found that 1) *E. coli* grew too slowly for sufficient yield under these conditions, and 2) the number of processing steps was untenable for translation to a GMP process. However, it was unclear if the iron oxide nanoparticle could be formed in *E. coli* naturally. First, it was attempted to cause the bacteria to incorporate iron from a medium enriched by adding ferric citrate, which mammalian cells normally would take up and incorporate into the ferritin core. Surprisingly, this did not result in any iron filled ferritin, which, discovered here, was because bacteria do not have the same mechanism for iron incorporation. Ferrous citrate was then chosen and resulted in the described invention. The molecule was then cationized and characterized as described. The advantage of this method is that it can be rapidly performed in GMP conditions with few steps, the iron oxide core can be detected by MRI, and the molecule can be modified to incorporate a radiolabel.

It was surprising and unexpected that the cationic fusion protein or the cationic protein itself would be capable of being radiolabeled due to its positively charged surface. As such, it was an initial concern that cationized ferritin and recombinant ferritin would not incorporate the radiolabel into the cationic core because of the cationic surface. Cu-64, for example, is also cationic, so there was concern that the radiolabel would experience charge repulsion. Under the correct synthesis conditions, however, it was demonstrated that it was possible to incorporate and purify the radiolabeled protein or fusion protein with no outer surface binding of the radiolabel. It was also discovered that the radiolabeled recombinant CF had similar physical properties (charge, shape, and hydrodynamic radius) as observed in non-radiolabeled CF. Because HrCF is 5 sticky (more than horse), amicon filters were used and saline was used rather than PBS for dialysis. Other methods are as described above for the radioCF imaging agent, unless noted otherwise.

What is claimed is:

1. An imaging agent comprising:
   a recombinant ferritin fusion protein comprising at least one heavy chain subunit of ferritin and at least one light chain subunit of ferritin; and
   a magnetic nanoparticle core, wherein the magnetic nanoparticle core is bound within the recombinant ferritin fusion protein.

2. The imaging agent of claim 1, wherein the imaging agent further comprises a positron emitting isotope bound within the recombinant ferritin fusion protein.

3. The imaging agent of claim 2, wherein the magnetic nanoparticle core comprises iron.

4. The imaging agent of claim 1, wherein the recombinant ferritin fusion protein is a human cationic recombinant ferritin fusion protein.

5. The imaging agent of claim 4, wherein the human cationic recombinant ferritin fusion protein comprises a cationic crosslinker selected from an amine ion and a $C_1$ to $C_{20}$ organic compound having one to four amine functional groups.

6. The imaging agent of claim 1, wherein the surface of the magnetic nanoparticle core or an inner surface of the recombinant ferritin fusion protein is radiolabeled with a radioisotope.

7. The imaging agent of claim 6, wherein the radioisotope is a synthetic radioisotope.

8. The imaging agent of claim 6, wherein the radioisotope is selected from $^{64}Cu$, $^{68}Ga$, $^{86}Y$, $^{89}Zr$, and $^{124}I$.

9. The imaging agent of claim 1, wherein the imaging agent is selected from a magnetic resonance imaging (MRI) contrast agent, a positron emission tomography (PET) imaging agent, a single-photon emission computerized tomography (SPECT) imaging agent, and a PET-MRI imaging agent.

10. The imaging agent of claim 1, wherein:
   the imaging agent has a diameter of about 30 nm or less, about 25 nm or less, about 20 nm or less, about 15 nm or less, about 14 nm or less, about 13 nm or less, about 12 nm or less, about 11 nm or less, or about 10 nm or less; or
   the magnetic nanoparticle core has a diameter of about 20 nm or less, about 15 nm or less, about 10 nm or less, about 5 nm or less, about 4 nm or less, about 3 nm or less, about 2 nm or less, or about 1 nm or less.

* * * * *